(12) United States Patent
Wang et al.

(10) Patent No.: US 9,943,608 B2
(45) Date of Patent: Apr. 17, 2018

(54) MULTI-ARM BIODEGRADABLE POLYMERS FOR NUCLEIC ACID DELIVERY

(71) Applicant: BAYLOR COLLEGE OF MEDICINE, Houston, TX (US)

(72) Inventors: Jin Wang, Sugar Land, TX (US); Fude Feng, Houston, TX (US)

(73) Assignee: BAYLOR COLLEGE OF MEDICINE, Houston, TX (US)

(*) Notice: Subject to any disclaimer, the term of this patent is extended or adjusted under 35 U.S.C. 154(b) by 0 days.

(21) Appl. No.: 14/442,557

(22) PCT Filed: Nov. 13, 2013

(86) PCT No.: PCT/US2013/069869
§ 371 (c)(1),
(2) Date: May 13, 2015

(87) PCT Pub. No.: WO2014/078399
PCT Pub. Date: May 22, 2014

(65) Prior Publication Data
US 2016/0279256 A1    Sep. 29, 2016

Related U.S. Application Data

(60) Provisional application No. 61/725,626, filed on Nov. 13, 2012.

(51) Int. Cl.
| | |
|---|---|
| C12N 15/11 | (2006.01) |
| A61K 47/48 | (2006.01) |
| A61K 47/42 | (2017.01) |
| A61K 9/00 | (2006.01) |
| C12N 15/113 | (2010.01) |
| A61K 47/64 | (2017.01) |
| A61K 47/69 | (2017.01) |
| A61K 48/00 | (2006.01) |

(52) U.S. Cl.
CPC ...... *A61K 47/48323* (2013.01); *A61K 9/0019* (2013.01); *A61K 47/42* (2013.01); *A61K 47/6455* (2017.08); *A61K 47/6935* (2017.08); *C12N 15/113* (2013.01); *A61K 48/00* (2013.01); *C12N 2310/122* (2013.01); *C12N 2310/14* (2013.01); *C12N 2310/141* (2013.01); *C12N 2310/351* (2013.01); *C12N 2310/531* (2013.01); *C12N 2320/32* (2013.01)

(58) Field of Classification Search
CPC ........................ C12N 15/113; A61K 47/48323
See application file for complete search history.

(56) References Cited

U.S. PATENT DOCUMENTS

| | | | |
|---|---|---|---|
| 8,546,487 B2 | 10/2013 | Kataoka et al. | |
| 2003/0232968 A1 | 12/2003 | Li et al. | |
| 2008/0249049 A1 | 10/2008 | Kataoka et al. | |
| 2009/0258416 A1 | 10/2009 | Kataoka et al. | |
| 2011/0256227 A1* | 10/2011 | Mirosevich | A61K 31/7105 424/490 |
| 2012/0053295 A1 | 3/2012 | Kataoka et al. | |

FOREIGN PATENT DOCUMENTS

WO    WO-2003/033027 A2    4/2003

OTHER PUBLICATIONS

Zhou et al. Adv. Mater. 2010, 22, 4567-4590.*
Mirosevich et al. Journal of Polymer Science 2012, 50, 836-850.*
Kim et al. Journal of Controlled Release 145 2010, 141-148.*
Neu et al. Gene Medicine 2005 7:992-1009.*
Takae et al. JACS 2008 130, 6001-6009.*
Itaka et al. Biomaterials 2010 31, 3707-3714.*
Ge et al. Biomaterials 2014 35, 3416-3426.*
International Search Report and Written Opinion for PCT/US2013/069869, dated Mar. 10, 2014.
International Preliminary Report on Patentability for PCT/US2013/069869, dated May 28, 2015.
Paleos, CM et al., "Molecular engineering of dendritic polymers and their application as drug and gene delivery systems", Molecular Pharmaceutics. Jan. 13, 2007. vol. 4, No. 2, pp. 169-188.
Zhang et al., "Novel poly(L-lysine) particles for gene delivery", Journal of controlled release : official journal of the Controlled Release Society 2011, 152 Suppl 1, e182.
Lollo et al., "Poly-L-lysine-based gene delivery systems. Synthesis, purification, and application", Methods in molecular medicine 2002, 69, 1.
Lim et al., "Development of a safe gene delivery system using biodegradable polymer, poly [a-(4-aminobutyl)-L-glycolic acid]", Journal of the American Chemical Society 2000, 122, 6524.
Wang et al., "Instability, stabilization, and formulation of liquid protein pharmaceuticals", International journal of pharmaceutics 1999, 185, 129.
Wright et al., "Nonenzymatic deamidation of asparaginyl and glutaminyl residues in proteins", Critical reviews in biochemistry and molecular biology 1991, 26, 1.
Brennan et al., "Effect of adjacent histidine and cysteine residues on the spontaneous degradation of asparaginyl- and aspartyl-containing peptides", International journal of peptide and protein research 1995, 45, 547.

(Continued)

*Primary Examiner* — Brian Whiteman
(74) *Attorney, Agent, or Firm* — Winstead PC

(57) ABSTRACT

In some embodiments, the present disclosure pertains to compositions for nucleic acid delivery into cells. In some embodiments, the composition comprises: (1) a cationic polymer unit comprising a plurality of polymeric arms, where the plurality of polymeric arms comprise poly(aspartic acid) derivatives; and (2) a nucleic acid associated with the cationic polymer unit. In some embodiments, the cationic polymer unit comprises a linker covalently associated with the plurality of polymeric arms. In some embodiments, the cationic polymer unit has a dendritic shape. In some embodiments, the cationic polymer unit has a star-like shape. In some embodiments, the cationic polymer unit is biodegradable. Further embodiments of the present disclosure pertain to methods of delivering a nucleic acid into cells by introducing into the cells one or more of the compositions of the present disclosure.

29 Claims, 17 Drawing Sheets

(56) References Cited

OTHER PUBLICATIONS

Geiger et al. "Deamidation, isomerization, and racemization at asparaginyl and aspartyl residues in peptides. Succinimide-linked reactions that contribute to protein degradation", The Journal of biological chemistry 1987, 262, 785.

Stephenson et al., "Succinimide formation from aspartyl and asparaginyl peptides as a model for the spontaneous degradation of proteins", The Journal of biological chemistry 1989, 264, 6164.

Catak et al., "Computational study on nonenzymatic peptide bond cleavage at asparagine and aspartic acid", The journal of physical chemistry. A 2008, 112, 8752.

Miyata et al., "Polyplexes from poly(aspartamide) bearing 1,2-diaminoethane side chains induce pH-selective, endosomal membrane destabilization with amplified transfection and negligible cytotoxicity", Journal of the American Chemical Society 2008, 130, 16287.

Pack et al., "Design and development of polymers for gene delivery", Nature reviews. Drug discovery 2005, 4, 581.

Hadjichristidis et al., "Synthesis of well-defined polypeptide-based materials via the ring-opening polymerization of alpha-amino acid N-carboxyanhydrides", Chemical reviews 2009, 109, 5528.

Wightman et al., "Different behavior of branched and linear polyethylenimine for gene delivery in vitro and in vivo", The journal of gene medicine 2001, 3, 362.

Mannisto et al., "Structure-activity relationships of poly(L-lysines): effects of pegylation and molecular shape on physicochemical and biological properties in gene delivery", Journal of controlled release : official journal of the Controlled Release Society 2002, 83, 169.

Zhao et al., Transfection of shRNA-encoding Minivector DNA of a few hundred base pairs to regulate gene expression in lymphoma cells, Gene Therapy, 2011, 18, 220.

Catanese et al., Supercoiled Minivector DNA resists shear forces associated with gene therapy delivery, Gene Therapy, 2012, 19, 94.

Liu et al., Nanoparticles of Compacted DNA Transfect Postmitotic Cells, Journal of Biological Chemistry, 2003, 278, 32578.

Boylan et al., Highly compacted DNA nanoparticles with low MW PEG coatings: In vitro, ex vivo and in vivo evaluation, Journal of Controlled Release, 2012, 157, 72.

Dai et al., Elucidating the interplay between DNA-condensing and free polycations in gene transfection through a mechanistic study of linear and branched PEI, Biomaterials (32), 2011, 8626-8634.

Yin et al., Reconfiguring the architectures of cationic helical polypeptides to control non-viral gene delivery, Biomaterials 34, 2013, 2340.

Wiseman, J.W., et al. "A comparison of linear and branched polyethylenimine (PEI) with DCChol/DOPE liposomes for gene delivery to epithelial cells in vitro and in vivo", (Gene Therapy (2003) 10, 1654-1662.

* cited by examiner

1, Liver; 2, spleen; 3, pancreas; 4, kidney; 5, ladder; 6, fat; 7, intestine; 8, stomach

MULTI-ARM BIODEGRADABLE POLYMERS FOR NUCLEIC ACID DELIVERY

CROSS-REFERENCE TO RELATED APPLICATIONS

This application claims priority to U.S. Provisional Patent Application No. 61/725,626, filed on Nov. 13, 2012. The entirety of the aforementioned application is incorporated herein by reference.

STATEMENT REGARDING FEDERALLY SPONSORED RESEARCH

Not applicable.

BACKGROUND

Current methods and compositions for delivering nucleic acids into cells suffer from numerous limitations, including toxicity, non-biodegradability, and transfection efficiency. Therefore, a need exists for new methods and compositions for delivering nucleic acids into cells.

SUMMARY

In some embodiments, the present disclosure pertains to compositions for nucleic acid delivery into cells. In some embodiments, the compositions comprise: (1) a cationic polymer unit comprising a plurality of polymeric arms, where the plurality of polymeric arms comprise poly(aspartic acid) derivatives; and (2) a nucleic acid associated with the cationic polymer unit.

In some embodiments, the cationic polymer unit comprises a linker associated with the plurality of polymeric arms. In some embodiments, the linker is covalently associated with the plurality of polymeric arms. In some embodiments, the cationic polymer unit has a dendritic shape. In some embodiments, the cationic polymer unit has a star-like shape. In some embodiments, the cationic polymer unit is biodegradable.

In some embodiments, the poly(aspartic acid) derivatives that make up the plurality of polymeric arms in the cationic polymer units of the present disclosure comprise from about 2 units to about 500 units of aspartic acid derivatives. In some embodiments, the poly(aspartic acid) derivatives comprise amine-modified aspartic acid derivatives (i.e., amine-modified poly(aspartic acid)). In some embodiments, the poly(aspartic acid) derivatives comprise diethylenetriamine-modified aspartic acid derivatives (PAsp(DET)$_n$), where n is an integer ranging from about 2 to about 500. In some embodiments, the poly(aspartic acid) derivatives include at least one of amine-modified poly(aspartic acid), (PAsp (DET)$_n$), where n ranges from about 2 to about 500, PAsp (DET)$_{100}$, PAsp(DET)$_{70}$, PAsp(DET)$_{200}$, and combinations thereof. In more specific embodiments, the plurality of polymeric arms comprise about 8 branches of PAsp(DET)$_{30}$ (i.e., 8-arm PAsp(DET)$_{30}$).

In some embodiments, the nucleic acid associated with the cationic polymer units of the present disclosure include at least one of DNA, RNA, siRNA, shRNA, miRNA, analogues thereof, and combinations thereof. In some embodiments, the nucleic acid associated with the cationic polymer units of the present disclosure include nucleic acid analogues, such as morpholinos modified nucleic acids and thiophosphate modified nucleic acids. In some embodiments, the nucleic acid is associated with the cationic polymer unit through electrostatic interactions.

Further embodiments of the present disclosure pertain to methods of delivering a nucleic acid into cells, where the method comprises introducing into the cells one or more of the compositions of the present disclosure. In some embodiments, the methods occur in vivo in a subject, such as a human being. In some embodiments, the methods occur in vitro.

DESCRIPTION OF THE FIGURES

FIG. 3 shows various data relating to gene suppression experiments.

DETAILED DESCRIPTION

Figure 1:
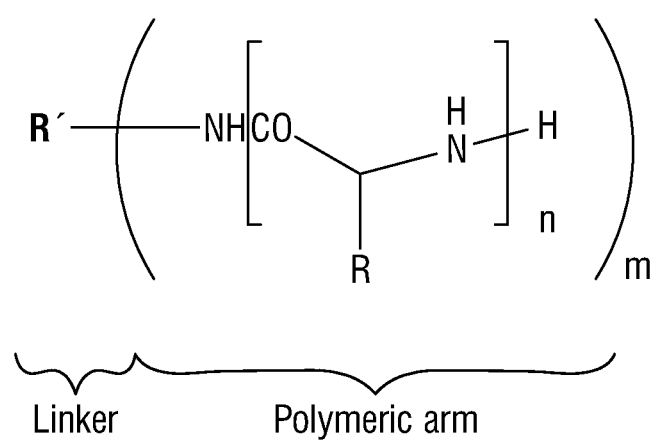
FIG. 1 provides the chemical structure of a cationic polymer unit with multiple polymeric arms. Letter n denotes the average repeat unit of each polymeric arm. Letter m denotes the number of polymeric arms.
Figure 2C:
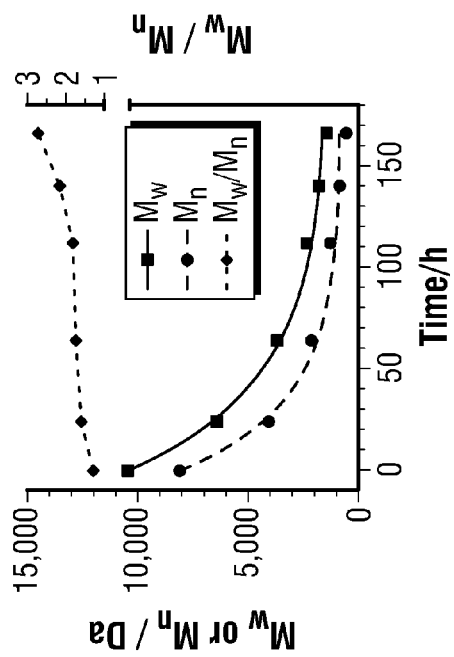
FIG. 2 provides data relating to the degradation of diethylenetriamine-modified poly(aspartic acid)$_{70}$ (PAsp (DET)$_{70}$) (also known as LP1) in a Tris buffer (pH=7.5). GPC traces of LP1 degradation products at different time points were monitored with refractive index (FIG. 2A) and light scattering detectors (FIG. 2B). Molecular weight ($M_w$ and $M_n$) analysis of the degradation products is also shown (FIG. 2C). The changes of $M_w$ and $M_n$ were fitted into mono-exponential decays. For traces with two peaks, only the major peak was analyzed for $M_w$ and $M_n$. A plot of log $(k_0/h^{-1})$ vs pH is also shown (FIG. 2D), where $k_0$ is the apparent first order degradation rate constant calculated based on $M_w$ and $M_n$.
Figure 2D:
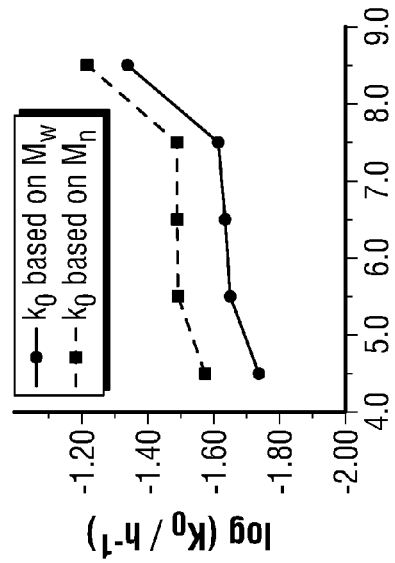
Figure 2A:
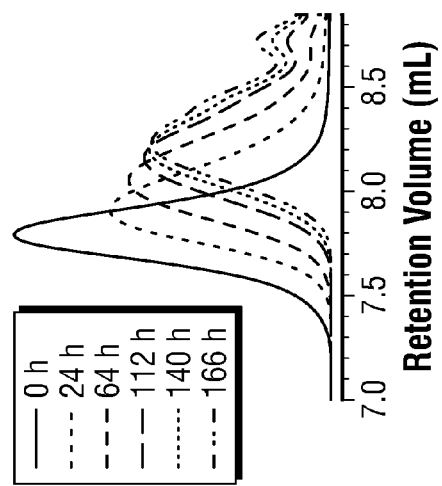
Figure 2B:
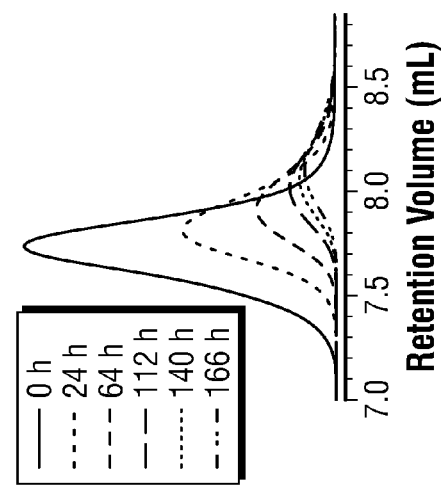

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

In recent years of biomedical applications, great attention has been paid to gene therapy for treating a variety of human diseases, such as genetic disorders, infections and cancers. However, the lack of effective and biocompatible non-viral gene carriers remains a big hurdle to apply gene therapy in clinical applications.

Great efforts have been made in studying synthetic non-viral vectors, such as cationic lipids and cationic polymers. Currently, the most widely used polymeric vector is based on the structure of poly(ethylenimine) (PEI) because PEI is inexpensive and can achieve high transfection efficiency. However, one major concern with PEI arises from its non-degradability and cytotoxicity. Though there are a number of published reports in synthesizing PEI derivatives in order to lower PEI cytotoxicity, these studies are still not able to resolve the issue of non-degradability.

Poly amino acids are attractive biomaterials due to the biocompatibility of the monomer building blocks. For instance, poly-L-lysine (PLL) has been intensively studied as a gene delivery carrier. However, due to the stable amide linkage and slow degradation in vivo, PLL is known for its long term toxicity. Strategies to degrade amide linkage under physiological conditions can broaden the application of PLL.

Asparagine is known to spontaneously and non-enzymatically deamidate into aspartic acid, which is usually related to protein aging and a major issue in the stabilization of therapeutic proteins in the pharmaceutical industry. Kataoka et al. developed a poly-asparagine analogue PAsp(DET)$_n$ as a gene delivery carrier (*Journal of the American Chemical Society*, 2008, 130, 16287). In PAsp(DET)$_n$, diethylenetriamine (DET) was used to substitute the amino group in the side chain of Asn. It was demonstrated that PAsp(DET)$_n$ showed both in vitro and in vivo transfection activity with minimal toxicity due to its biodegradability. However, the mechanism accounting for this spontaneous degradation of PAsp(DET)$_n$ has not been well understood.

Additional polymers have also been developed for gene delivery. Architecture of polymers is an important parameter in determining the delivery efficacy. For instance, Wagner et al. extensively compared the different behavior of branched and linear polyethylenimine (PEI) for gene delivery in vitro and in vivo (*The journal of gene medicine* 2001, 3, 362). Urtti et al. demonstrated that gene delivery efficiency is dependent on the architecture of poly-L-lysine used (*Journal of controlled release: official journal of the Controlled Release Society* 2002, 83, 169). It also has been shown that star shaped oligoethylenimine achieved higher in vitro transfection efficiency and lower cytotoxicity compared to branched 25K PEI, the gold standard used in biology for in vivo transfection (*The journal of gene medicine* 2001, 3, 362). Building on Kataoka's previous success of asparagine based polymers, Applicants decided to explore how the architecture of Asn based polymers affects gene delivery efficiency.

In some embodiments, the present disclosure pertains to compositions for nucleic acid delivery into cells. In some embodiments, the composition includes: (1) a cationic polymer unit that includes a plurality of polymeric arms; and (2) a nucleic acid associated with the cationic polymer unit. In some embodiments, the plurality of polymeric arms include Asn based polymers, such as polymers that include derivatives of aspartic acid (i.e., poly(aspartic acid) derivatives). Further embodiments of the present disclosure pertain to methods of utilizing the compositions of the present disclosure for nucleic acid delivery into cells.

Compositions

In some embodiments, the compositions of the present disclosure have an N/P ratio from about 1 to about 40. In some embodiments, the compositions of the present disclosure have an N/P ratio of about 5. In some embodiments, the compositions of the present disclosure have an N/P ratio of about 10. In various embodiments, the compositions of the present disclosure have N/P ratios of about 1, 2, 3, 5 or 10. In some embodiments, the compositions of the present disclosure are biodegradable.

As set forth in more detail herein, the compositions of the present disclosure can have various types of cationic polymer units, various types of polymeric arms, and various types of nucleic acids. Moreover, various methods may be utilized to deliver the compositions of the present disclosure into various types of cells.

Cationic Polymer Units

In the present disclosure, cationic polymer units generally refer to cationic chemical structures that include a plurality of polymeric arms. An example of a cationic polymer unit is shown in FIG. 1.

In some embodiments (as illustrated in FIG. 1), the cationic polymer units of the present disclosure include a linker that is associated with a plurality of polymeric arms. In some embodiments, the linker is covalently associated with a plurality of polymeric arms. In some embodiments, the linker is non-covalently associated with a plurality of polymeric arms through various types of interactions, such as ionic interactions, acid-base interactions, hydrogen bonding interactions, pi-stacking interactions, van der Waals interactions, adsorption, physisorption, self-assembly, sequestration, hydrophobic interactions, and combinations thereof.

In some embodiments, the linker is a chemical structure with multiple functional groups (e.g., amine groups) that can covalently couple to polymers. In some embodiments, linkers may include small molecules, macromolecules, nanoparticles and combinations thereof. In some embodiments, linkers may include a nanoparticle, such as a nanoparticle functionalized with a plurality of functional groups. In some embodiments, the functional groups may include at least one of amine groups, hydroxyl groups, carboxylic acid groups, azide groups, thiol groups, carbonyl groups, alkyne groups, alkene groups, halogens, activated esters, and combinations thereof.

The cationic polymer units of the present disclosure can have various types of shapes when associated with polymeric arms. For instance, in some embodiments, the cationic polymer units of the present disclosure have dendritic shapes. In some embodiments, the cationic polymer units of the present disclosure have star-like shapes. In some embodiments, the cationic polymer units of the present disclosure have brush-like or comb-like shapes. In some embodiments, the cationic polymer units of the present disclosure have circular shapes. In some embodiments, the cationic polymer units of the present disclosure have combinations of one or more of the above shapes. For instance, in some embodiments, the cationic polymer units of the present disclosure have hybrid structures that include a star-like shape and a brush-like shape.

The cationic polymer units of the present disclosure may also have various molecular weights. For instance, in some embodiments, the cationic polymer units of the present disclosure may have a molecular weight ($M_n$) ranging from about 1 kDa to about 500 kDa. Moreover, the cationic polymer units of the present disclosure may be associated with various types of polymeric arms.

Polymeric Arms

In the present disclosure, polymeric arms generally refer to individual polymers that are associated with cationic polymer units. In some embodiments, the polymeric arms of the present disclosure include polypeptides, such as polypeptides derived from cationic amino acids, cationic amino acid derivatives, and combinations thereof. In some embodiments, the cationic amino acids and cationic amino acid derivatives may include at least one of lysine, ornithine, histidine, arginine, serine, threonine, cysteine, aspartic acid, glutamic acid, tyrosine, 2,4-diaminobutyric acid, and combinations thereof. In some embodiments, the polymeric arms of the present disclosure include a biodegradable polypeptide backbone with pendant cationic side chains.

In more specific embodiments, the polymeric arms may include Asn based polymers. In some embodiments, the polymeric arms of the present disclosure include derivatives of aspartic acid (i.e., poly(aspartic acid) derivatives). In some embodiments, the poly(aspartic acid) derivatives in the polymeric arms include multiple units of aspartic acid derivatives. In some embodiments, the polymeric arms include from about 2 units to about 500 units of aspartic acid derivatives.

The poly(aspartic acid) derivatives of the present disclosure may contain various types of aspartic acid derivatives. For instance, in some embodiments, the poly(aspartic acid) derivatives include aspartic acids that have been modified with amine groups (i.e., amine-modified poly(aspartic acid)s). In some embodiments, the poly(aspartic acid) derivatives include aspartic acids that have been modified with guanidyl groups. In some embodiments, the poly(aspartic acid) derivatives include aspartic acids that have been modified with sulfonium groups. In some embodiments, the poly(aspartic acid) derivatives include aspartic acids that have been modified with phosphonium groups. In some embodiments, the poly(aspartic acid) derivatives include aspartic acids that have been modified with diethylenetriamine (i.e., diethylenetriamine-modified poly(aspartic acid)s or (PAsp(DET)$_n$)). In some embodiments, n is an integer ranging from about 2 to about 500. In some embodiments, n is an integer ranging from about 2 to about 100.

In some embodiments, the poly(aspartic acid) derivatives may include at least one of amine-modified poly(aspartic acid); PAsp(DET)$_n$, where n ranges from about 2 to about 500, PAsp(DET)$_{100}$, PAsp(DET)$_{70}$, and combinations thereof.

The cationic polymer units of the present disclosure may be associated with a number of polymeric arms. For instance, in some embodiments, the cationic polymer units of the present disclosure may include from about 3 polymeric arms to about 200 polymeric arms. In some embodiments, the cationic polymer units of the present disclosure may include from about 3 polymeric arms to about 50 polymeric arms. In some embodiments, the cationic polymer units of the present disclosure include at least about 32 polymeric arms. In some embodiments, the cationic polymer units of the present disclosure include at least about 8 polymeric arms. In some embodiments, the cationic polymer units of the present disclosure include about 8 polymeric arms. In more specific embodiments, the cationic polymer units of the present disclosure are associated with 8 polymeric arms of PAsp(DET)$_{30}$ (i.e., 8-arm PAsp(DET)$_{30}$).

Nucleic Acids

The cationic polymer units of the present disclosure may also be associated with various types of nucleic acids. For instance, in some embodiments, the nucleic acids may include at least one of DNA, shRNA, RNA, siRNA, miRNA, analogues thereof, and combinations thereof. In some embodiments, the nucleic acid associated with the cationic polymer units of the present disclosure include nucleic acid analogues, such as morpholinos modified nucleic acids and thiophosphate modified nucleic acids. In more specific embodiments, the nucleic acids may include plasmid DNA. In some embodiments, the nucleic acids may include a gene. In some embodiments, the gene may include, without limitation, GFP, luciferase, beta-GAL, VEGF, HER-2, SRC-3, HIF-1, and combinations thereof.

The nucleic acids of the present disclosure may be associated with cationic polymer units through various types of interactions. For instance, in some embodiments, the nucleic acids of the present disclosure may be associated with cationic polymer units through electrostatic interactions. In some embodiments, the nucleic acids of the present disclosure may be associated with cationic polymer units through ionic interactions, acid-base interactions, hydrogen bonding interactions, pi-stacking interactions, van der Waals interactions, adsorption, physisorption, self-assembly, sequestration, hydrophobic interaction, and combinations thereof.

Nucleic Acid Delivery into Cells

Additional embodiments of the present disclosure pertain to methods of delivering a nucleic acid into cells by introducing one or more of the aforementioned compositions into the cells. Various methods may be utilized to deliver the compositions of the present disclosure into various types of cells. Moreover, the methods of the present disclosure may occur both in vitro and in vivo.

In Vivo Delivery of Nucleic Acids

In some embodiments, the methods of the present disclosure may occur in vivo. For instance, in some embodiments, the compositions of the present disclosure may be used to deliver nucleic acids into the cells of a subject.

The compositions of the present disclosure may be introduced into the cells of various subjects. In some embodiments, the subject is a human being. In additional embodiments, the subjects may be non-human animals, such as mice, rats, other rodents, or larger mammals, such as dogs, monkeys, pigs, cattle and horses.

The compositions of the present disclosure can be introduced into the cells of subjects by various modes of administration. For instance, in some embodiments, the compositions of the present disclosure can be administered by oral administration (including gavage), inhalation, subcutaneous administration (sub-q), intravenous administration (I.V.), intraperitoneal administration (I.P.), intramuscular administration (I.M.), intrathecal injection, intratracheal injection, ocular injection, intradermal injection, intracardiac injection, intrathoracic injection, intracerebral injection, and combinations of such modes. In some embodiments, the compositions of the present disclosure can be administered by topical application (e.g., transderm, ointments, creams, salves, eye drops, and the like). Additional modes of administration can also be envisioned.

The compositions of the present disclosure may also be administered in a single dose or multiple doses throughout a time period. For instance, in some embodiments, the compositions of the present disclosure may be administered to a subject in two separate doses.

In addition, the compositions of the present disclosure may be administered to localized sites in a subject, such as a tissue or vasculature. For instance, the compositions of the present disclosure may be injected directly into a site of a tumor in a subject.

In Vitro Delivery of Nucleic Acids

In some embodiments, the methods of the present disclosure may occur in vitro. For instance, in some embodiments, the compositions of the present disclosure may be used to deliver nucleic acids into cells that are isolated or grown in vitro.

Various methods may also be used to deliver nucleic acids into cells in vitro. For instance, in some embodiments, the compositions of the present disclosure may be introduced into cells in vitro by transfection. In some embodiments, the compositions of the present disclosure may be introduced into cells in vitro by transfection in combination with transposons.

Cells

The methods of the present disclosure may be utilized to deliver nucleic acids into various types of cells. For instance, in some embodiments, the methods of the present disclosure are utilized to deliver the compositions of the present disclosure into tumor cells. In some embodiments, the methods of the present disclosure are utilized to deliver the compositions of the present disclosure into stem cells. In some embodiments, the methods of the present disclosure are utilized to deliver the compositions of the present disclosure into immune cells, such as dendritic cells, macrophages, lymphocytes, T cells, and the like. In some embodiments, the methods of the present disclosure are utilized to deliver the compositions of the present disclosure into any dividing and non-dividing cells.

Applications and Advantages

In some embodiments, the present disclosure provides a new class of polypeptide-based polymers for delivery of nucleic acids into cells. In some embodiments, the compositions of the present disclosure can be used to deliver nucleic acids into cells in a highly efficient manner with low cytotoxicity. As such, the compositions of the present disclosure can find applications in numerous fields, such as cancer therapy, gene therapy, vaccine development, clinical research, basic research, and combinations thereof.

Additional Embodiments

Reference will now be made to more specific embodiments of the present disclosure and experimental results that provide support for such embodiments. However, Applicants note that the disclosure herein is for illustrative purposes only and is not intended to limit the scope of the claimed subject matter in any way.

Example 1. Synthesis of Linear PBLAs

The synthesis of linear PBLAs is illustrated in Scheme 1. To a solution of BLA-NCA (1.0 mmol) in anhydrous DMSO (2 mL) was added BocNH-EG3-NH2 (0.01 mmol for L-PBLA1, or 0.004 mmol for L-PBLA2) in anhydrous DMSO (2 mL) under nitrogen flow. After reaction of 3 days, the reaction mixture was added dropwise into dry diethyl ether (100 mL). Next, the solid was collected and dried. The degree of polymerization of L-PBLA1 was estimated to 70 based on 1H NMR ($M_n$=14.4 KDa). The degree of polymerization of L-PBLA2 was estimated to 200 based on 1H NMR (Mn=41.1 KDa). $^1$H NMR (400 MHz, DMSO-d6) for L-PBLAs: 8.18 (br), 7.25 (br), 5.0 (br), 4.6 (m), 2.8 (br), 2.8 (m), 1.3 (s).

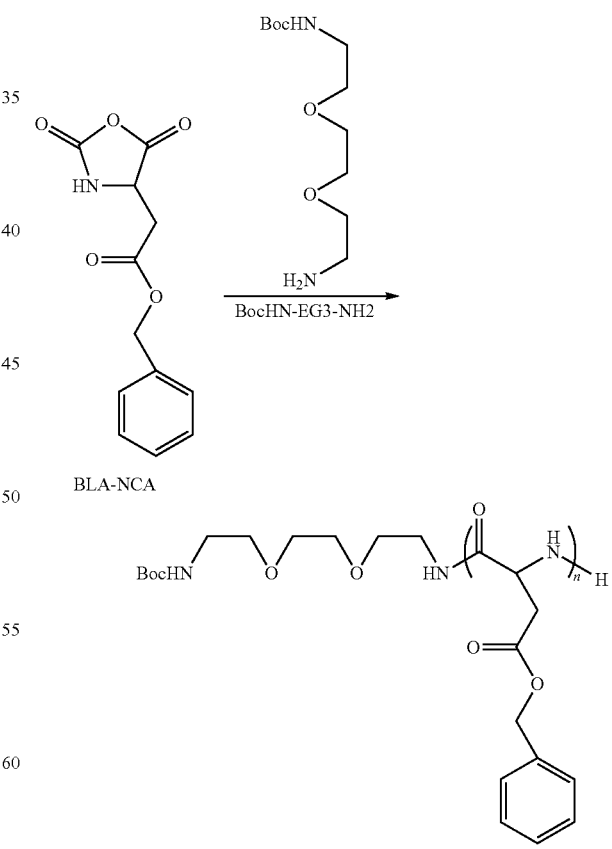

Scheme 1. Synthesis of liner PBLAs.

Example 2. Synthesis of Cationic Linear Polymers LP1 and LP2

The synthesis of LP1 and LP2 is illustrated in Scheme 2. The solution of linear L-PBLA1 or L-PBLA2 (1.0 eq) in NMP was mixed with a solution of diethylenetriamine (50 eq) in NMP at 0° C. and stirred for 1 h. The mixture was added dropwise into HCl (5 M) to result in full neutralization, dialyzed against HCl (0.02 M) and subsequent water for 3 days, and then lyophilized to give the target product as a white solid. $^1$H NMR (400 MHz, D$_2$O) for LP1: 3.58 (br), 3.38 (br), 3.22 (br), 2.91 (br), 1.47 (s). $^1$H NMR (400 MHz, D$_2$O) for LP2: 3.58-3.38 (br), 3.21 (br), 2.95 (br), 2.79 (br).

Scheme 2. Synthesis of LP1 and LP2.

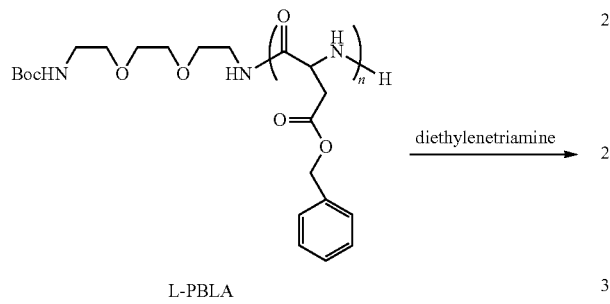

L-PBLA

→ diethylenetriamine

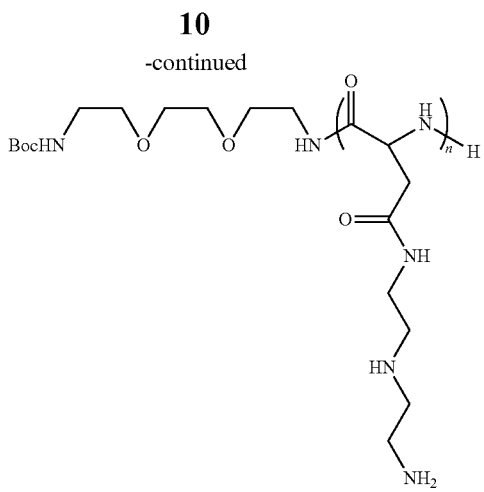

LP1, n = 70
LP2, n = 200

Example 3. Synthesis of SP-PBLA

The synthesis of SP-PBLA is illustrated in Scheme 3. To a solution of BLA-NCA (1.0 mmol) in anhydrous DMSO (2 mL) was added BocNH-EG3-NH2 (4.2 µmol) in anhydrous DMSO (2 mL) under nitrogen flow. After reaction of 3 days, the reaction mixture was added dropwise into dry diethyl ether (100 mL). Next, the solid was collected and dried. The degree of polymerization of each arm was estimated to 30 based on GPC analysis ($M_w$=50.6 kDa, $M_n$=43.5 KDa, $M_w/M_n$=1.16).

Scheme 3. Synthesis of SP-PBLA.

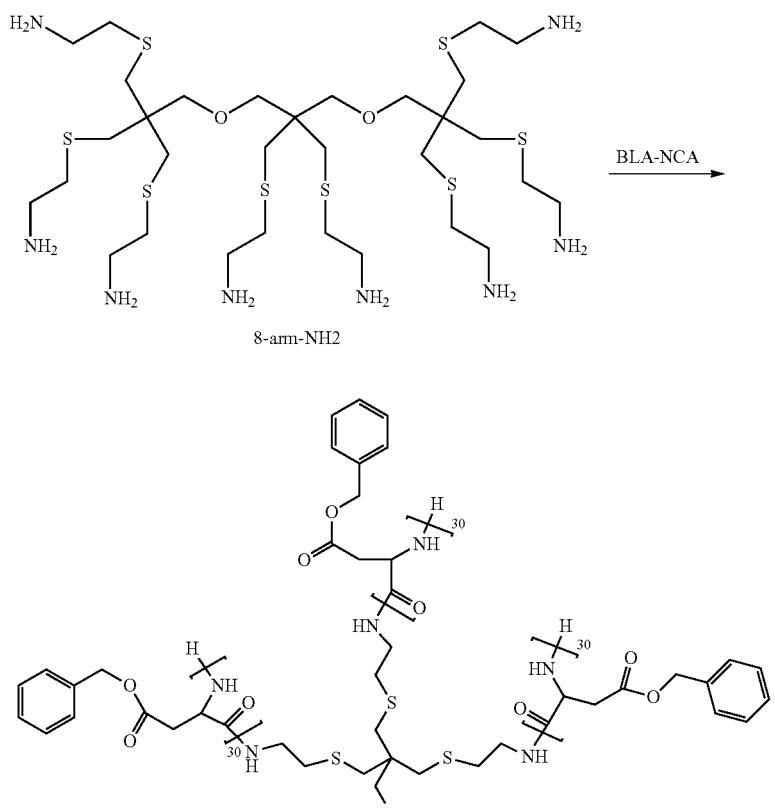

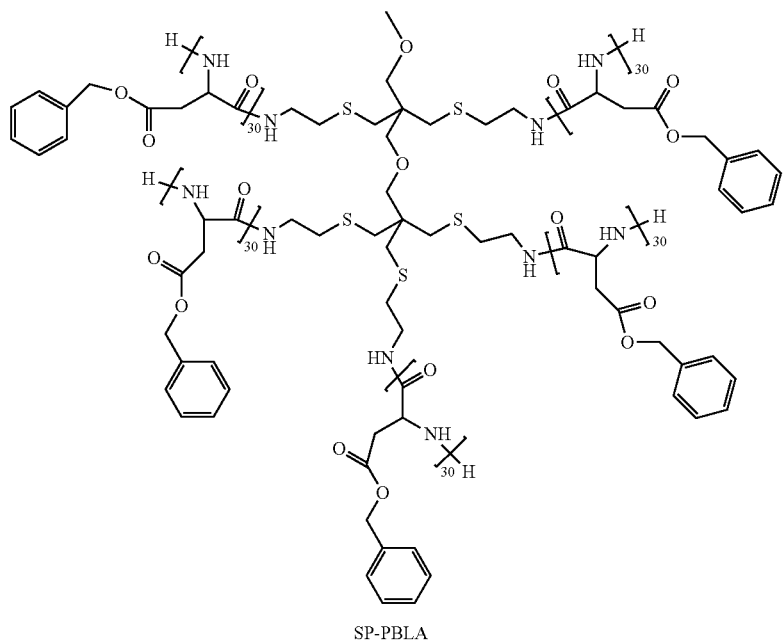

SP-PBLA

Example 4. Synthesis of Branched Polymer SP

The synthesis of SP is illustrated in Scheme 4. The solution of SP-PBLA (1.0 eq) in NMP was mixed with a solution of diethylenetriamine (400 eq) in NMP at 0° C. and stirred for 1 h. The mixture was added dropwise into HCl (5 M) to result in full neutralization, dialyzed against HCl (0.02 M) and subsequent water for 3 days, and then lyophilized to give the target product as a white solid.

Scheme 4. Synthesis of SP.

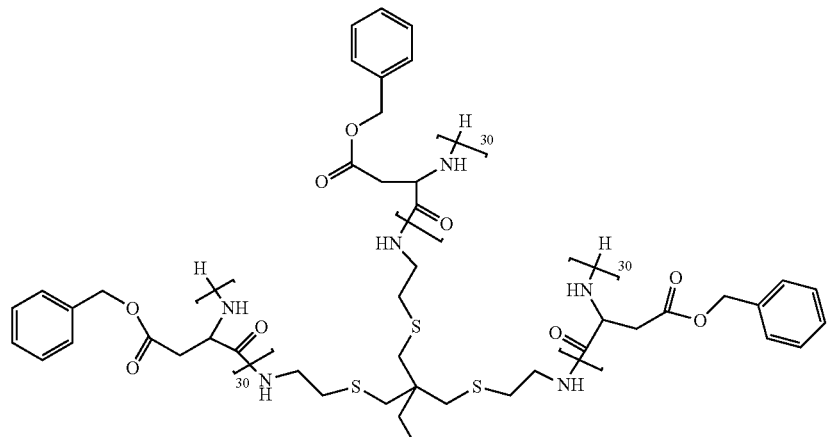

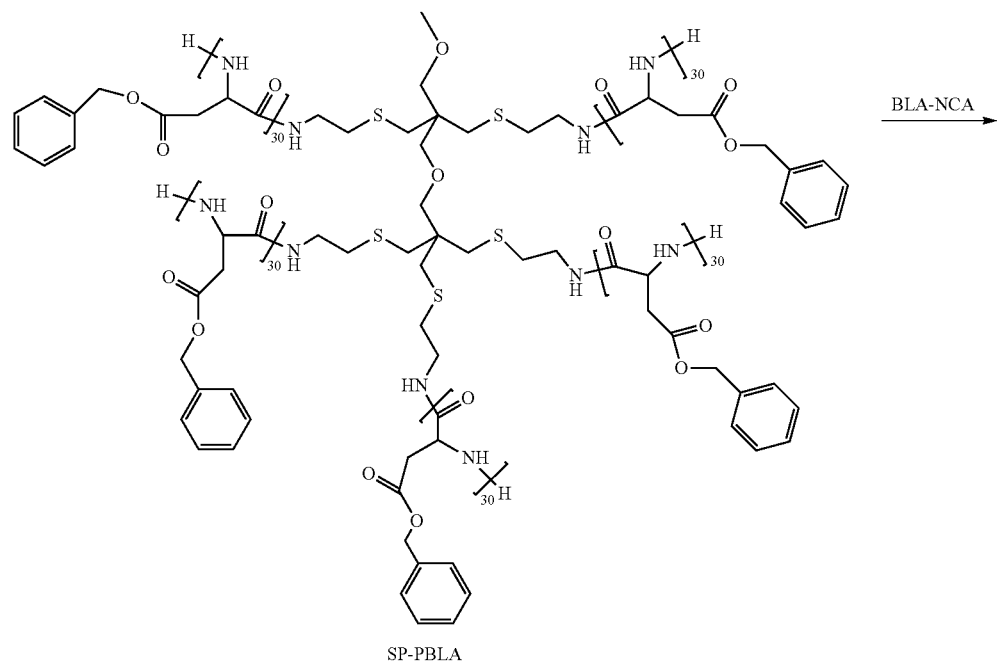
SP-PBLA
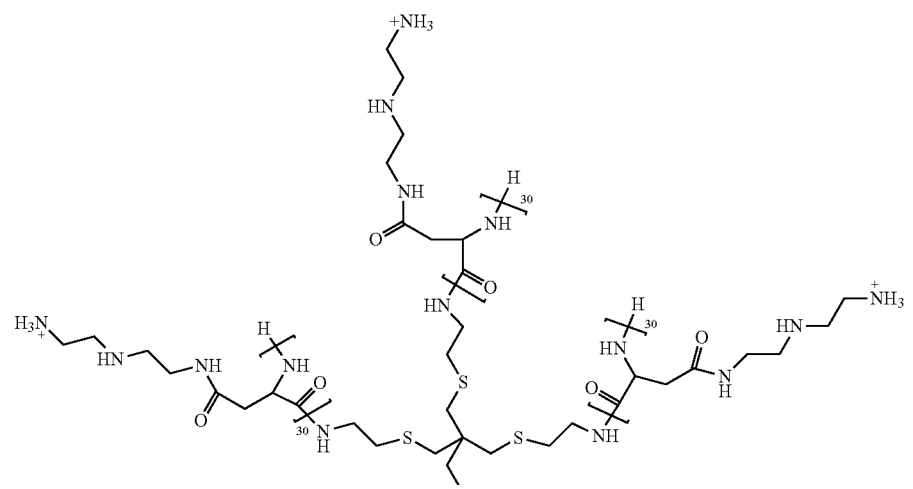

-continued

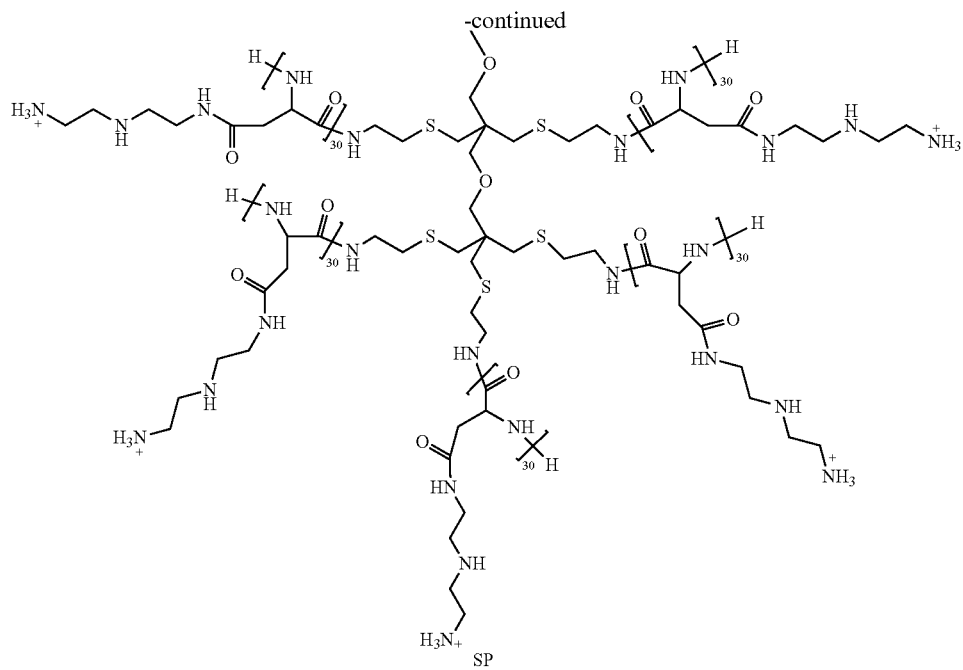

SP

Example 5. Degradation of LP1

LP1 was incubated in buffers at varying pH values (4.5~8.5) at 37° C. Small portions at certain incubation times were taken out for GPC measurements. The degradation results are shown in FIG. 2.

Example 6. Cell Transfection and Cell Toxicity Assays

The following polymer compositions were delivered to cells: 8-arm PAsp(DET)$_{30}$ (also known as SP); PAsp(DET)$_{70}$ (also known as LP1), PAsp(DET)$_{200}$ (LP2) and PEI. Table 1 below provides various properties relating to LP1, LP2 and SP.

TABLE 1

Molecular weight estimates for LP1, LP2 and SP based on GPC measurements. The buffer (1% HAcO/0.1M NaNO$_3$/NaN$_3$) was used as the solvent for GPC measurements.

| Polymer | Architecture | Mn by GPC | Mw by GPC | PDI |
|---|---|---|---|---|
| LP1 | linear | 10.9 KDa | 12.6 KDa | 1.16 |
| LP2 | linear | 29.7 KDa | 35.0 KDa | 1.18 |
| SP | 8-arm | 38.0 KDa | 45.6 KDa | 1.20 |

Each of the polymer compositions were dissolved in water (5 mg/mL) and mixed gently with shRNA-encoded plasmid DNA (600 ng for each well) with varying N/P ratios and incubated at 4° C. for 1 h. The solutions were then diluted with DMEM buffer to 50 and then added into wells containing 100 μL H1299 cell culturing medium. After 4.5 h of incubation at 37° C., the medium was replaced with 10% FBS/DMEM and incubated for 42 h. The cells were digested and pooled for cytometry measurements.

The toxicity of various polymer containing samples to cells was assayed. The results shown in FIG. 8 were obtained by using a standard colorimetry-based MTT.

Figure 8:
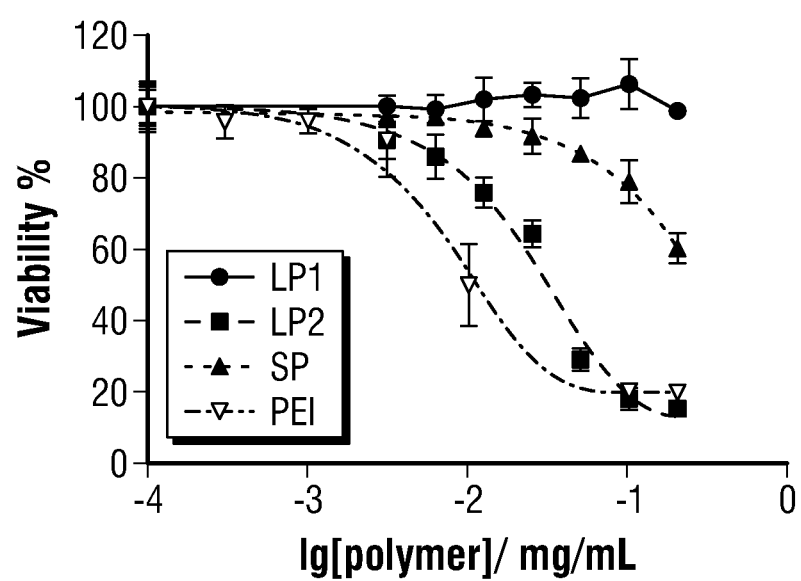
FIG. 8 shows toxicities of free polymers of LP1, LP2, SP and PEI on H1299 cells after 24 hours of incubation.

For instance, FIG. 8 shows toxicities of free polymers of LP1, LP2, SP and PEI on H1299 cells after 24 hours of incubation in an MTT assay. The MTT assay demonstrates low cytotoxicity of SP at concentrations up to 0.1 mg/mL. These results are in sharp contrast to the high cytotoxicity of PEI.

Example 7. GFP Knockdown Assay

Figure 3A:
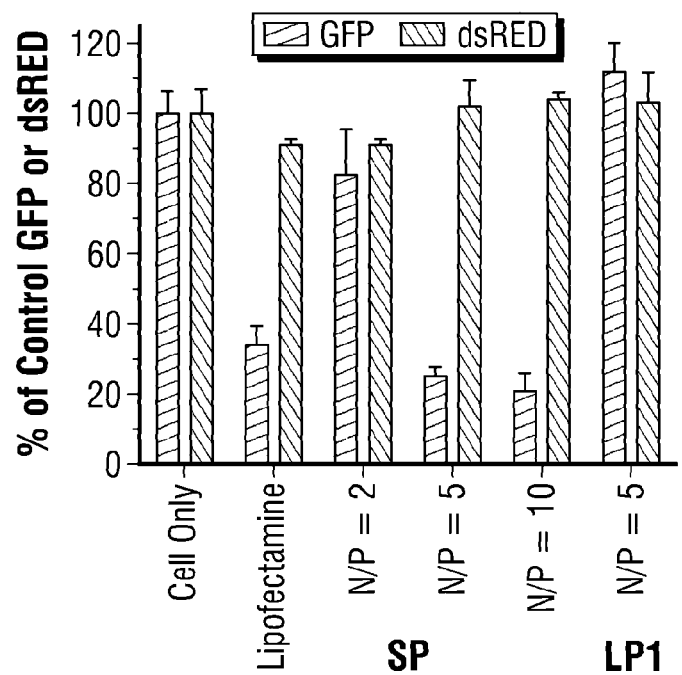
FIG. 3A shows GFP protein knockdown on GFP expressing H1299 cells. A plasmid expressing shRNA against GFP (600 ng per well) is delivered by lipofectamine 2000, 8-arm PAsp(DET)$_{30}$ (also known as SP) (N/P=2, 5 and 10), and LP1 (N/P=5). dsRED protein is an internal control for nonspecific knockdown.
Figure 3B:
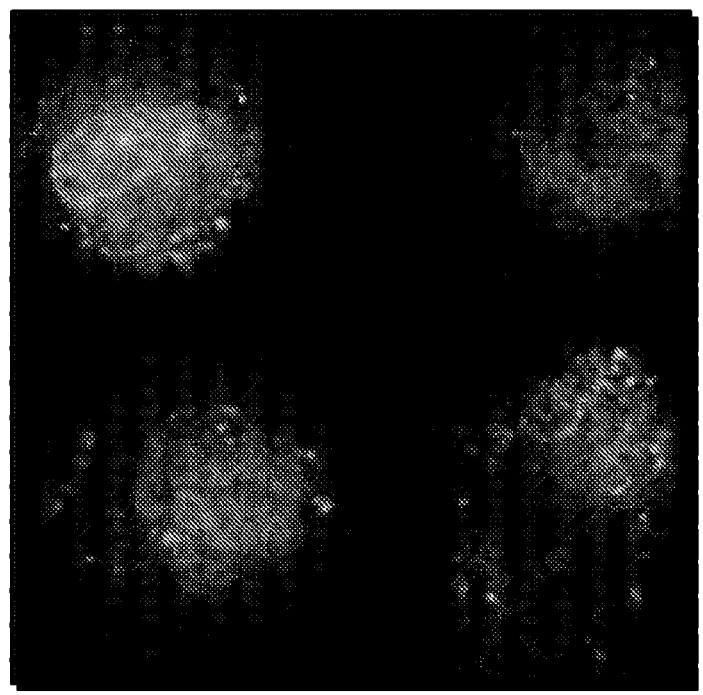
FIG. 3B shows confocal microscopy of the above nanoparticles. The image indicates that the nanoparticles formed by SP and plasmid (green) entered the nucleus (stained with DAPI, blue) of H1299 cells.

A GFP knockdown assay was performed by delivery of plasmid DNA along with various polymer compositions into GFP-expressed H1299 cells. The plasmid DNA encoded a shRNA sequence targeting a GFP gene. The results are shown in FIG. 3. The results show that the transfection efficiency by SP/plasmid DNA is comparable to commercially available lipofectamine at N/P ratios of 5 or 10. In contrast, there is no detectable knockdown of GFP protein by linear LP1/plasmid DNA.

Example 8. DLS and Zeta Potential Measurements

Figure 4:
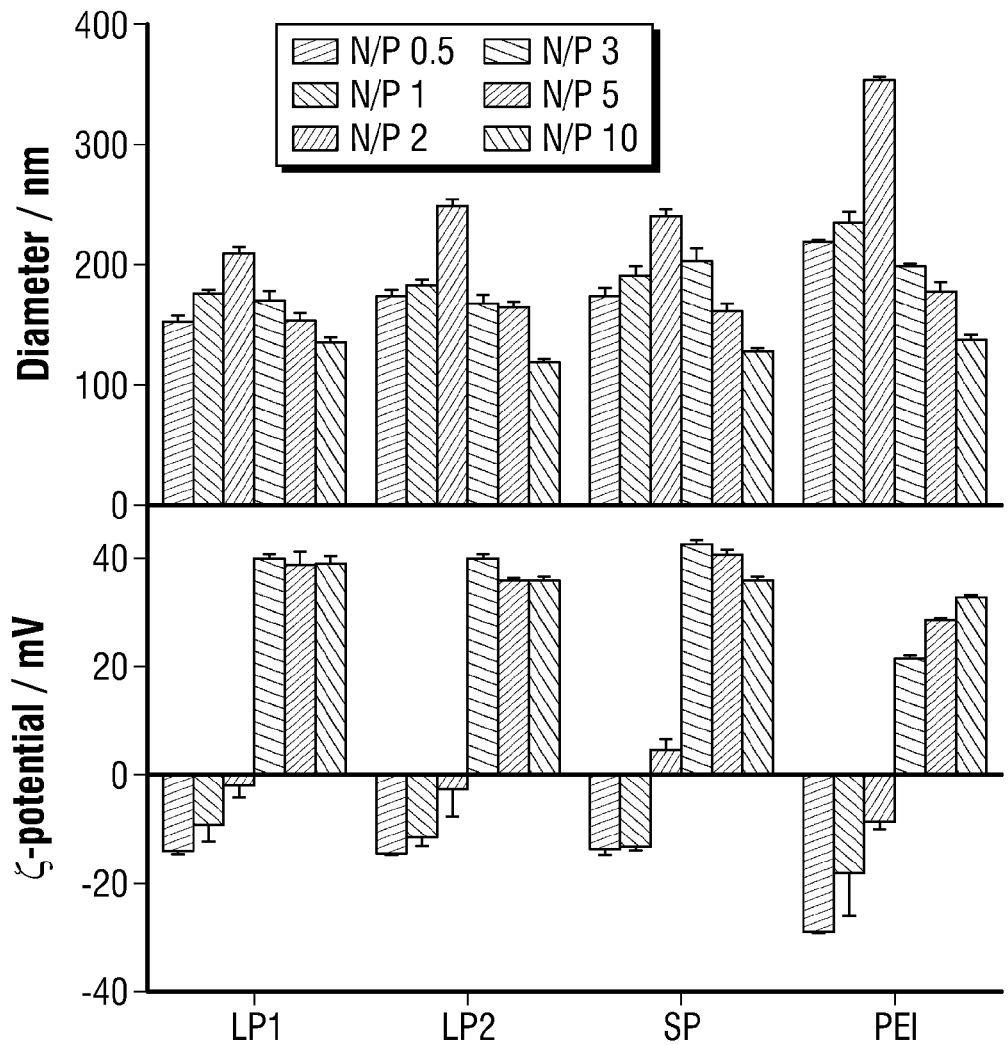
FIG. 4 shows characterization of polyplex nanoparticles for SP, LP1, LP2 (PAsp(DET)$_{200}$), and PEI by Dynamic Light Scattering (DLS) and zeta-potential measurements on a Malvern Zetasizer.

Polyplex nanoparticles were prepared by mixing SP, LP1, LP2, and PEI with plasmid pGFP at varying N/P ratios. The size and charge properties of polyplex nanoparticles were characterized by Dynamic Light Scattering (DLS) spectroscopy and zeta potential measurements, which were achieved on a Malvern Nanosizer ZS (Malvern, USA) equipped with a 633 nm laser. As illustrated in FIG. 4, the polyplex nanoparticles are shown to have hydrodynamic diameters smaller than 200 nm in DI-water and zeta potentials higher than 30 mV when the N/P ratio is greater than 3.

Example 9. Imaging of Polyplex Nanoparticles by Transmission Electron Microscopy (TEM)

Figure 5:
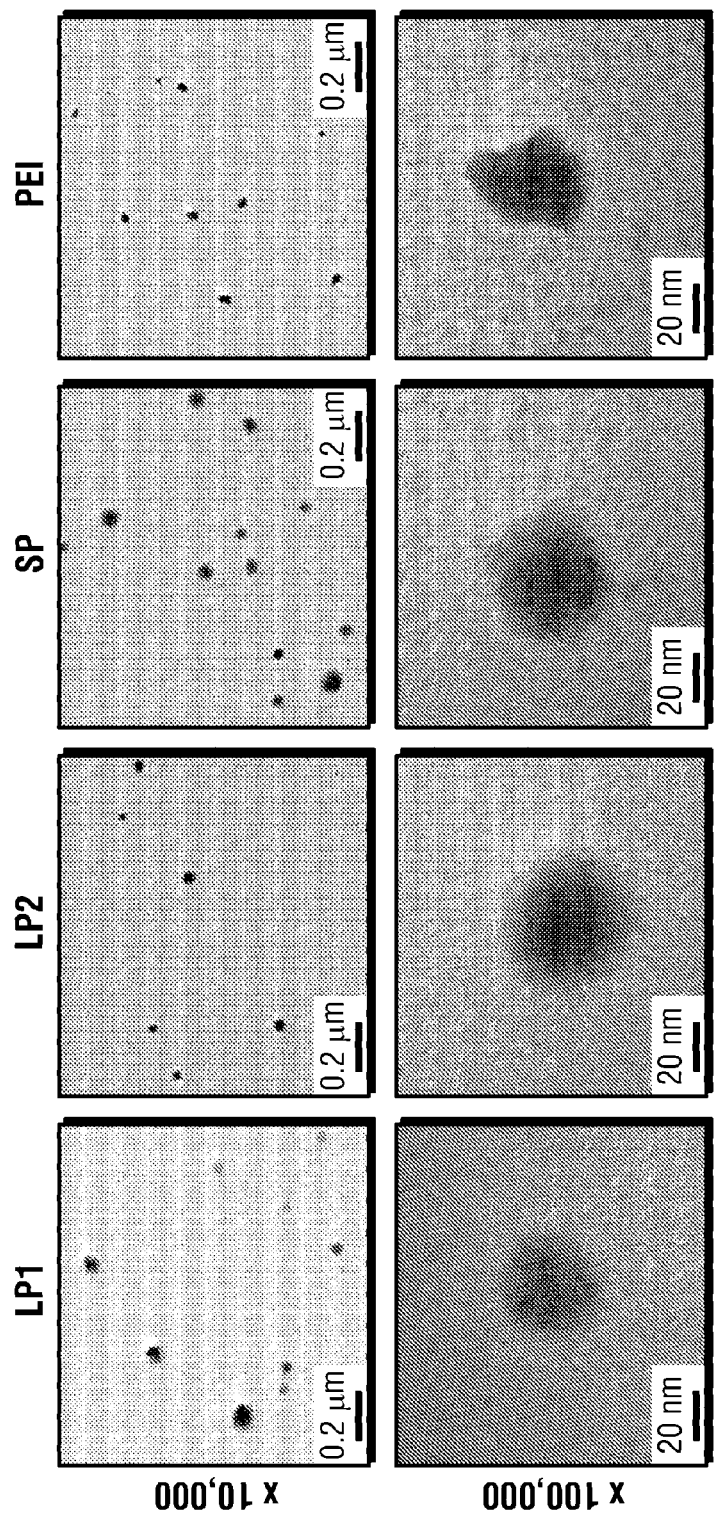
FIG. 5 shows images of polyplex nanoparticles for SP, LP1, LP2 and PEI (N/P 5) stained with 0.8% uranyl acetate by transmission electronic microscopy (TEM). Scale bars: 200 nm (top row) and 20 nm (bottom row).

Polyplex nanoparticles prepared at N/P ratios of 5 from Example 8 were diluted with DI-water to a final pGFP concentration of 40 μg/mL, applied for 10 min in 6 μL onto the carbon surface of 400 mesh copper electron microscope grids (Teda Pella, covered with Formvar and carbon films), washed with water, stained by uranyl acetate (0.8% in methanol, freshly filtered on 20 nm Whatman membrane), and examined on a Hitachi TEM instrument at a magnification of 10,000×~100,000×. The images were saved in .TIFF format and treated with Image J software (version 1.46r). As illustrated in FIG. 5, the polyplex nanoparticles are spherically shaped with dehydrated diameters smaller than 100 nm on average.

Example 10. Gel Retardation Assays

Figure 6A:
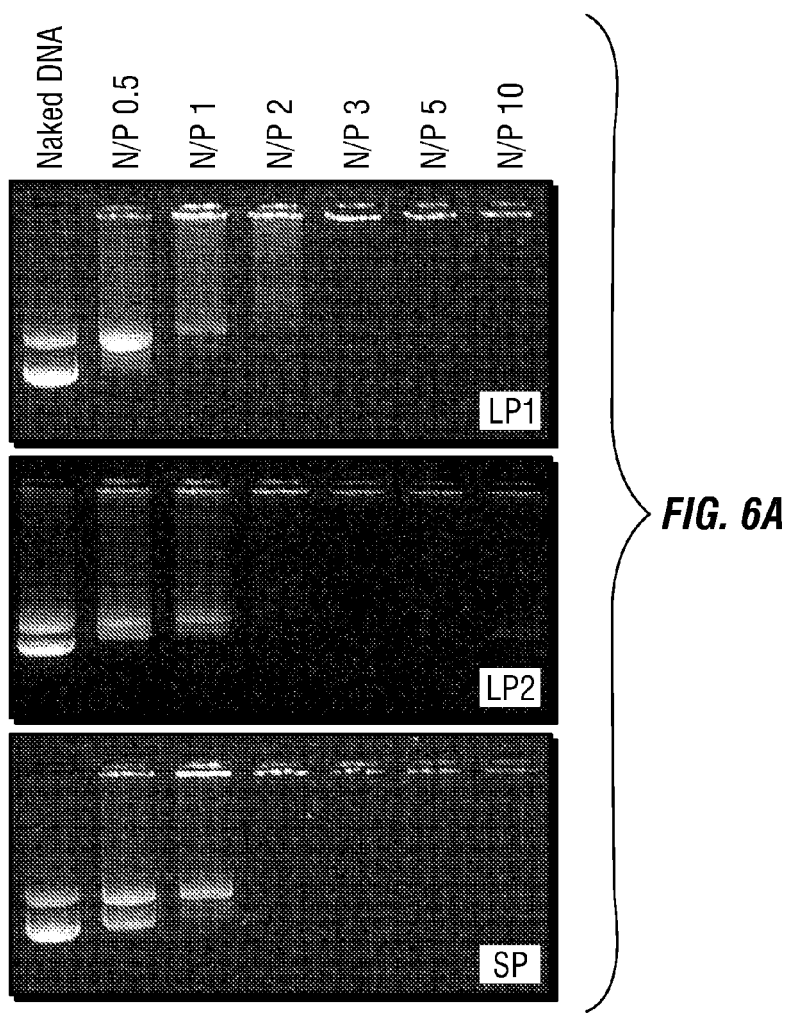
FIG. 6 shows agarose gel electrophoresis of LP1, LP2, and SP at different N/P ratios (FIG. 6A) and their corresponding condensing percentages (FIG. 6B). The gels were stained with ethidium bromide (EB) and imaged using a UVP gel documentation system.
Figure 6B:
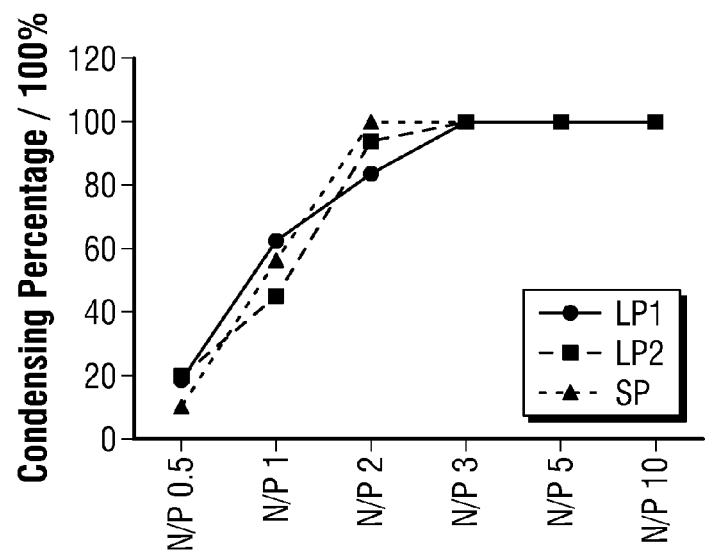

Polyplex nanoparticles were prepared by mixing LP1, LP2, SP and branched PEI (25 KDa) and pGFP in water at desired N/P ratios (0.5, 1, 2, 3, 5, and 10). Gel electrophoresis was performed using EB pre-stained 0.8% TAE agarose gel (Bio-Rad) under 100 V constant voltage for 45 min. Gels were imaged using a UVP gel documentation system equipped with a digital camera. The results are shown in FIG. 6. The results show that, at N/P 2, the plasmid is completely retarded for LP2 and SP.

Example 11. Heparin Competition Assays

Figure 7A:
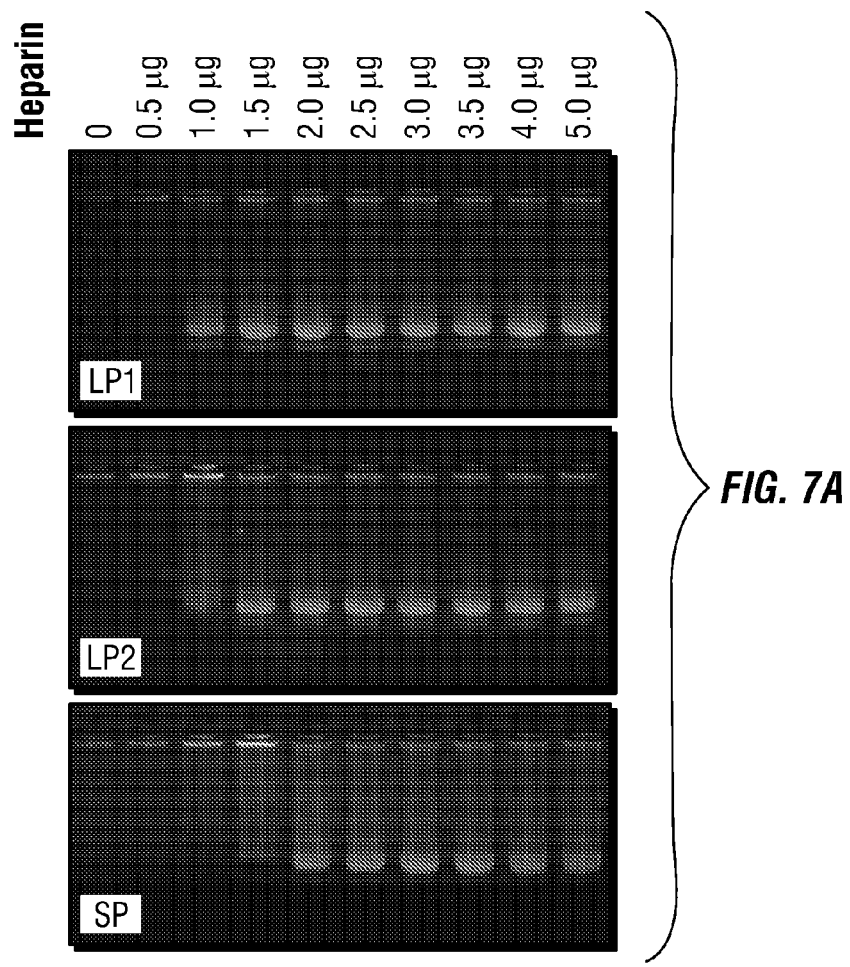
FIG. 7 shows agarose gel electrophoresis results of heparin competition assays with polyplex nanoparticles for LP1, LP2 and SP at N/P ratios of 5 (FIG. 7A) and their corresponding release percentages (FIG. 7B).
Figure 7B:
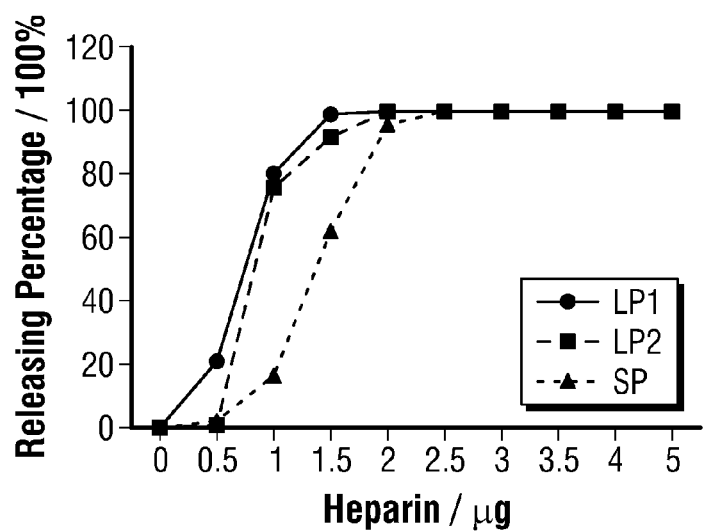

Polyplex nanoparticles were prepared by mixing each polymer (LP1, LP2, SP and PEI) and pGFP (480 ng) prepared at N/P 5 with aqueous heparin solutions (0~5 µg) in a final volume of 10 µL at room temperature for 20 min, followed by gel electrophoresis on EB pre-stained 0.8% agarose gel in 1×TAE buffer. The gel was run at 150 V for 40 min, stained with EB and imaged using a UVP gel documentation system. The results are shown in FIG. 7. The electrophoresis result reflects the condensing capability of polymers with plasmid in the order of: SP≈PEI>LP2>LP1. The results suggest that multi-arm structured polymers are more effective than their linear counterparts in condensing capability.

Example 12. Stability of Polyplex Nanoparticles in Serum and PBS

Figure 9A:
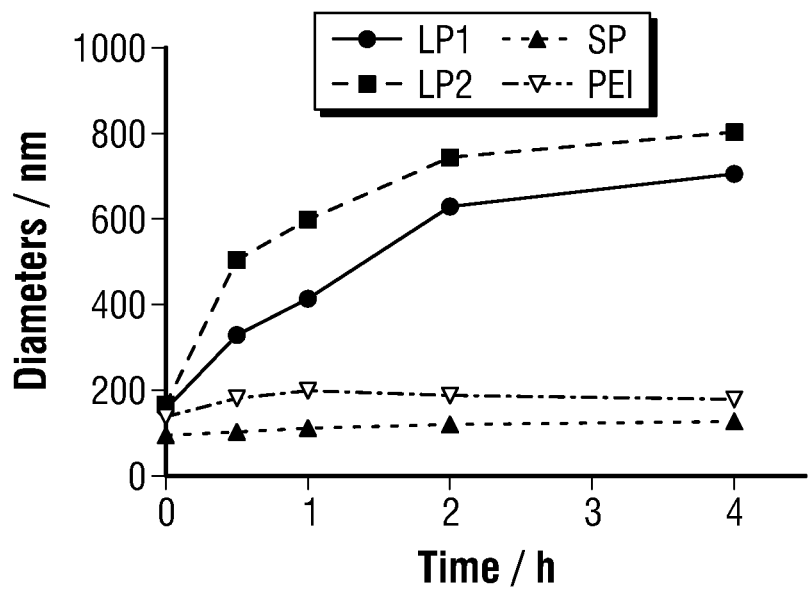
FIG. 9 shows the stability of polyplex nanoparticles for LP1, LP2, SP and PEI at N/P ratios of 10 in PBS (FIG. 9A) and fetal bovine serum (FIG. 9B).

Polyplex nanoparticle solutions for LP1, LP2, SP and PEI were prepared at N/P ratios of 10 and incubated with PBS at a total pEGFP concentration of 10 µg/mL. The average hydrodynamic diameters were monitored by DLS measurements at desired time points for a total period of 4 hours. As illustrated in FIG. 9A, significant aggregation occurred for LP1 and LP2 particles. However, the branched polymers (SP and PEI) displayed good stability in PBS without forming aggregates.

Figure 9B:
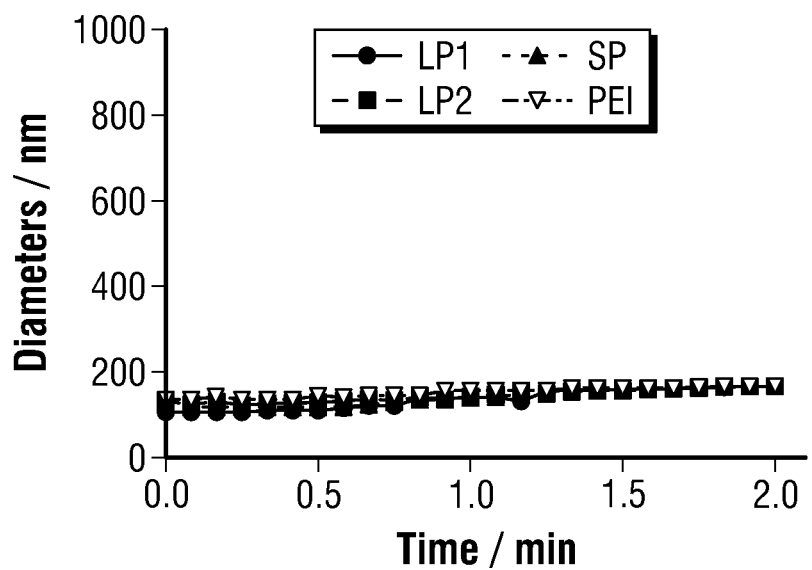

Polyplex nanoparticle solutions for LP1, LP2, SP and PEI were prepared at N/P ratios of 10 and incubated with 20% of fetal bovine serum at a total pGFP concentration of 10 µg/mL. The average hydrodynamic diameters were monitored by DLS measurements at 5-min intervals for a total period of 2 hours. As illustrated in FIG. 9B, all of the tested polymers exhibit high stability in serum without forming aggregates.

Example 13. In Vitro pGFP Transfection

Figure 10:
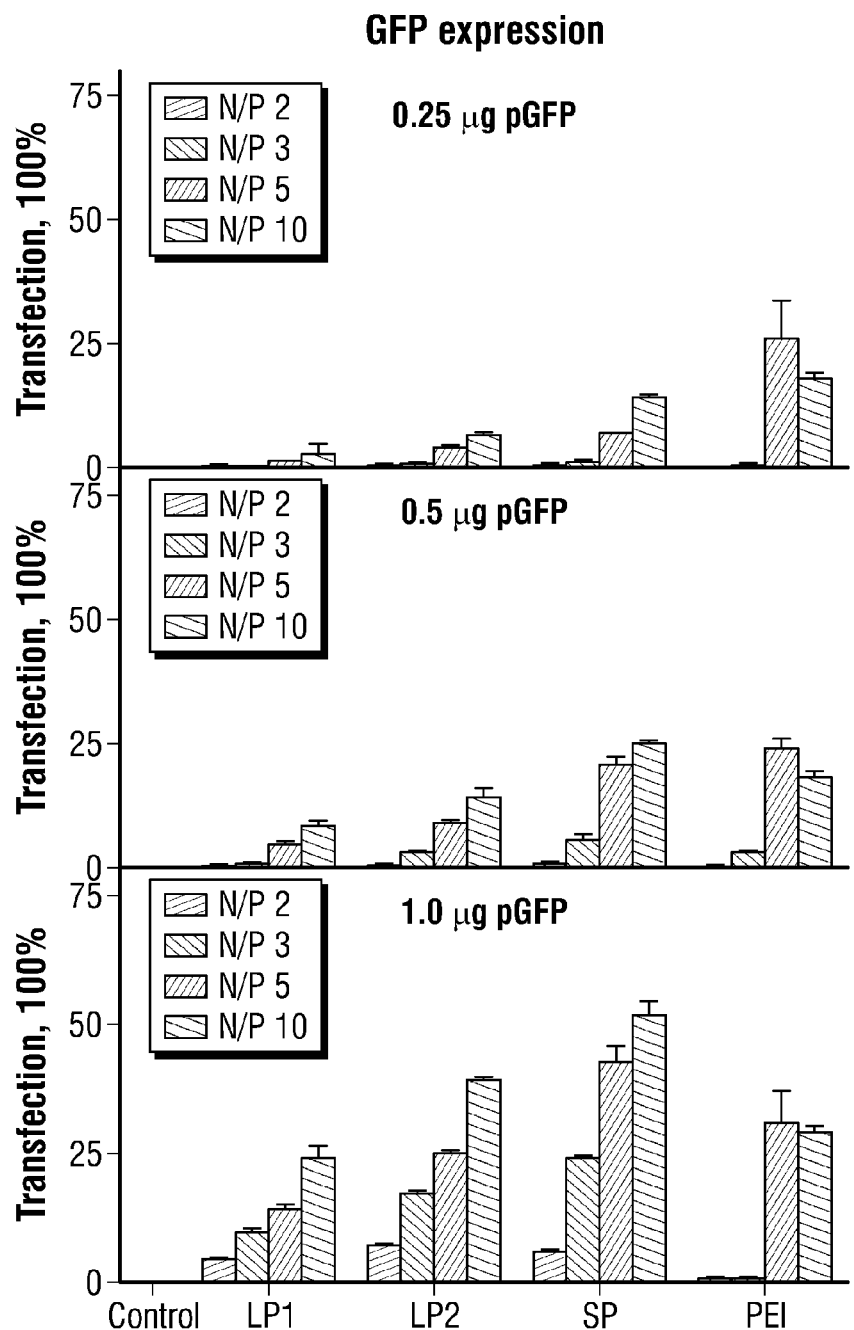
FIG. 10 shows in vitro GFP transfection assays via fluorescence assisted cell sorting (FACS) analyses for polyplex nanoparticles for LP1, LP2, SP and PEI at various N/P ratios.

The pGFP transfection assay was performed by delivery of pGFP into H1299 cells with polyplex nanoparticles prepared by mixing each cationic polymer (LP1, LP2, SP and PEI) and plasmid DNA at desired N/P ratios. H1299 cells were transfected with the polyplex nanoparticles at various N/P ratios and plasmid doses in serum-free medium for 4 h followed by additional 40 h incubation in 10% FBS-supplemented medium. GFP expression was then examined by flow cytometry. Based on the percentage of transfected cells, FACS results shown in FIG. 10 demonstrate increasing transfection capability in the following order: LP1<LP2<SP≈PEI.

Example 14. In Vitro pMV-CMV-Luc2 Transfection

Figure 11:
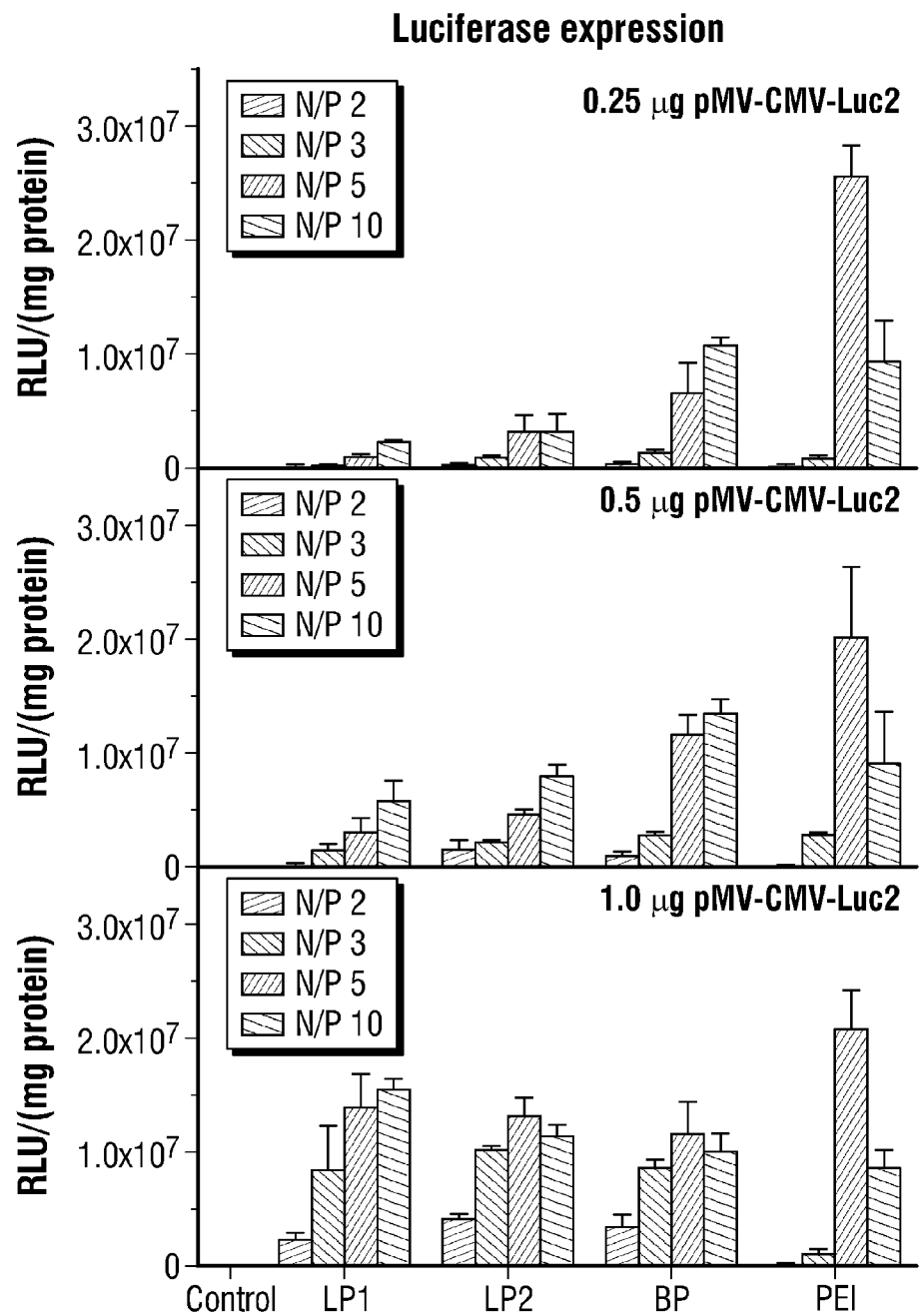
FIG. 11 shows in vitro luciferase transfection via luciferase luminescence assays for polyplex nanoparticles for LP1, LP2, SP and PEI at various N/P ratios.

The pMV-CMV-Luc2 transfection assay was performed by delivery of plasmid pMV-CMV-Luc2 into H1299 cells with polyplex nanoparticles prepared by mixing each cationic polymer (LP1, LP2, SP and PEI) and plasmid DNA at desired N/P ratios. H1299 cells were transfected with the polymer/pMV-CMV-Luc2 nanoparticles in serum-free medium for 4 h followed by additional 40 h incubation in 10% FBS-supplemented medium. GFP expression was then examined by flow cytometry. The results are shown in FIG. 11. Based on luminescence intensity, luciferase luminescence assay results demonstrate increasing transfection capability in the following order: LP1<LP2<SP≈PEI, especially when low dose of plasmid is used.

Example 15. In Vitro Cell Uptake Assay

Figure 12A:
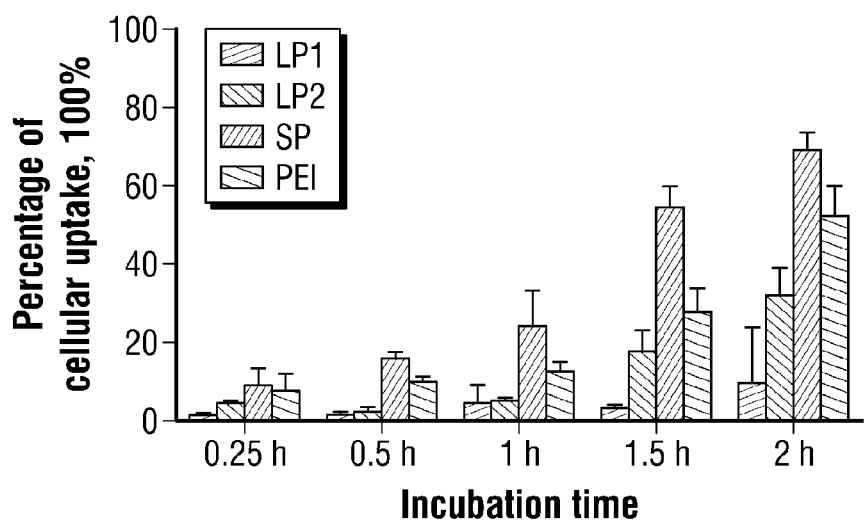
FIG. 12 shows cellular uptake of polyplex nanoparticles via FACS assays for LP1, LP2, SP and PEI. The results are shown in chart (FIG. 12A) and graph (FIG. 12B) formats.
Figure 12B:
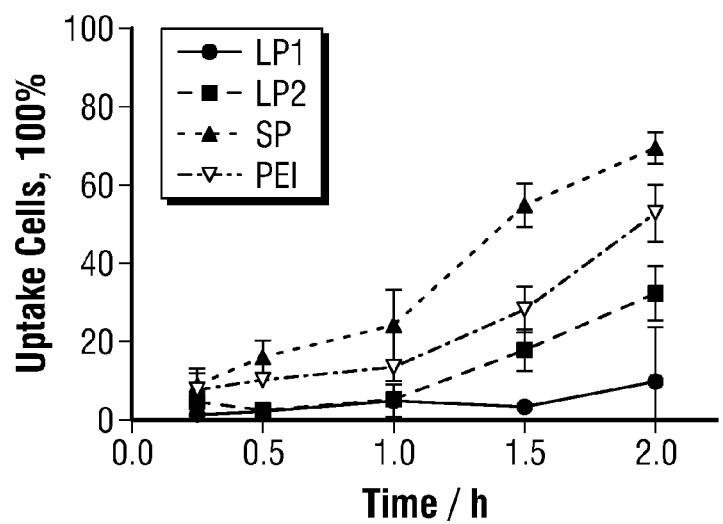

Plasmid pMV-CMV-Luc2 was labeled with Rhodamine by using a Minis Label it kit. The labeled plasmid was then mixed with non-labeled pMV-CMV-Luc2 at a 1:1 ratio and then complexed with cationic polymers (LP1, LP2, SP and PEI) to form Rhodamine-labeled nanoparticles at N/P ratios of 10. H1299 cells (without GFP expression) were incubated for 15 min, 0.5 h, 1 h, 1.5 h and 2 h with Rhodamine-labeled particles containing 0.2 µg pGFP/well (100 µL) in serum-free medium. After trypsinization, the cells were harvested and subjected to FACS analysis. The results are summarized in FIG. 12. The FACS data indicate that the cellular uptake rate within 2 hours is strongly polymer-dependent and increases in the following order: LP1<LP2<PEI<SP.

Example 16. In Vivo Transfection by Intravenous Injection

Figure 13A:
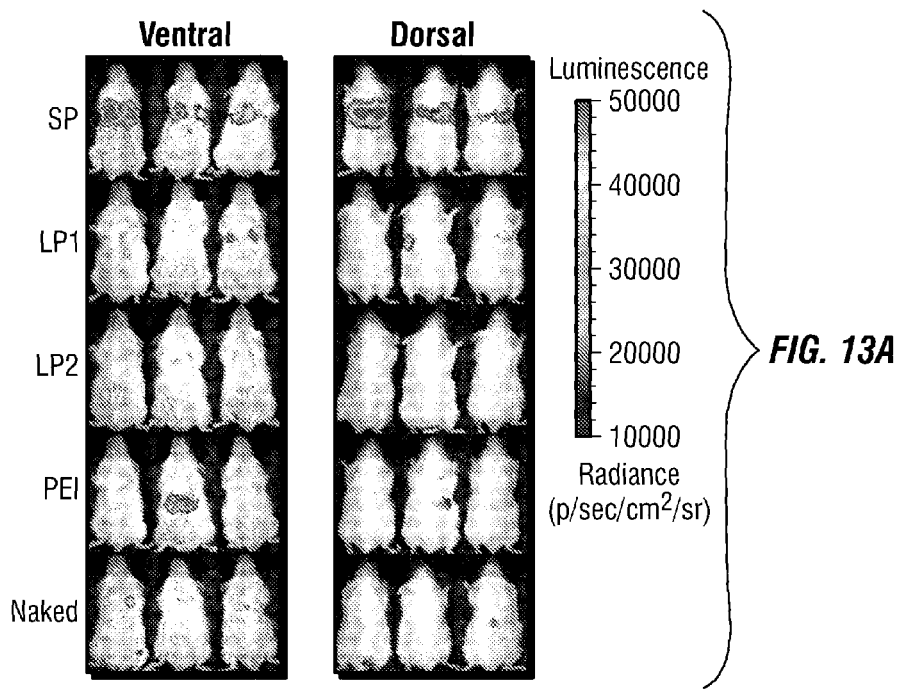
FIG. 13 shows in vivo images (FIG. 13A) and tissue images (FIG. 13B) from mice injected with polyplex nanoparticles at 24 h post administration for LP1, LP2, SP and PEI at N/P ratios of 10.
Figure 13B:
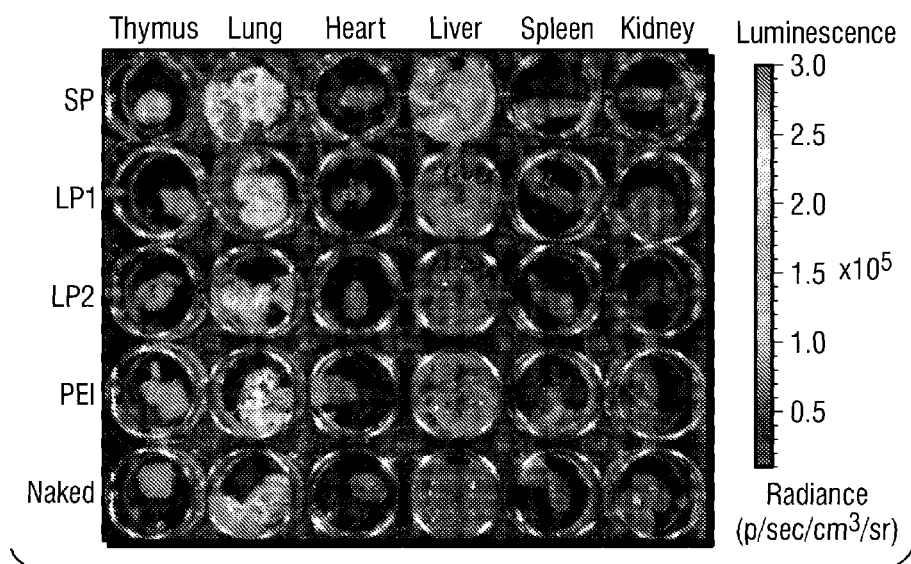
Figure 14:
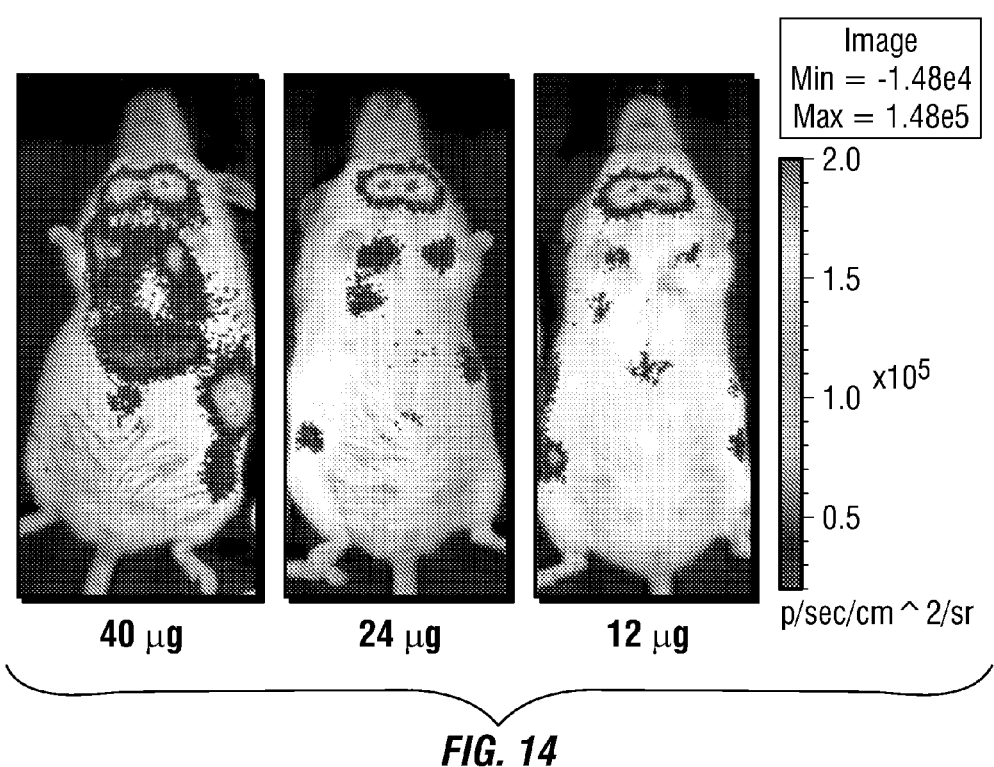
FIG. 14 shows in vivo imaging of mice at 4 h post intravenous injection of SP/pMV-CMV-Luc2 particles with different dosages of plasmid DNA.

Swiss Webster Mice (~7 weeks old, purchased from Harland, USA) were intravenously injected with pMV-CMV-Luc2 alone or with polyplex nanoparticle solutions (LP1, LP2, PEI and SP) prepared at N/P ratios of 10. The plasmid was dosed at 40 µg (or 12 µg, 24 µg). After 24 h, mice were intravenously injected with D-luciferin (200 µL, 12.5 mg/mL, 2.5 mg/mouse), anesthetized with 2.5% isoflurane, and imaged using an IVIS 100 imaging system. After euthanization, the organs were removed and imaged. The results are summarized in FIG. 13. The imaging data indicate that SP/pMV-CMV-Luc2 efficiently transfects the lungs of mice with much higher efficiency than other tested polymers. Observation of luciferase expression in thymus for SP/pMV-CMV-Luc2 delivery at 4 h post administration is shown in FIG. 14. The results suggest efficient transfection of immune cells by SP/pMV-CMV-Luc2. The imaging data also indicate that the luciferase expression in thymus is saturated, even though the plasmid was dosed as low as 12 µg.

Example 17. In Vivo Transfection by Intracardiac Injection

Figure 15:
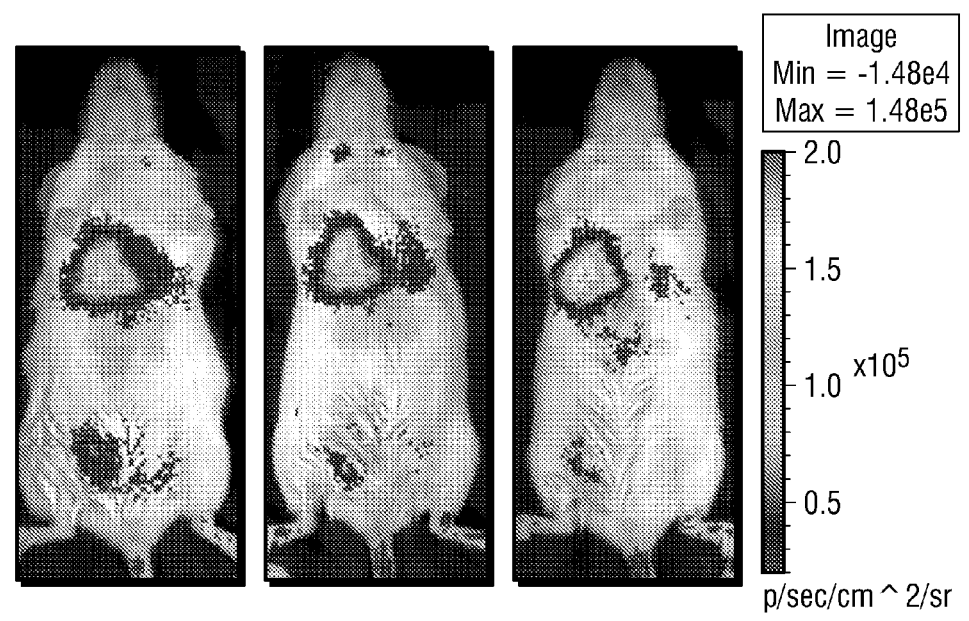
FIG. 15 shows in vivo imaging of mice that received intracardiac injection with SP/pMV-CMV-Luc2 (N/P 10, 40 µg). The images were taken at 24 h post administration.

The mice from Example 16 were anesthetized by intraperitoneal injection with 1.25% Avertin (0.6~0.7 mL, prepared by dissolving 0.5 g of tribromoethanol in 1 mL of tertiary amyl alcohol followed by 10 times dilution in PBS and filtration on a 0.2 µm cellulose membrane). The furs of the mice were shaven at the chest. A total volume of 100 µL of polyplex solution prepared by mixing SP and pMV-CMV-Luc2 (40 µg) at N/P 10 was injected slowly into the left ventricle of the heart. The injected mice were placed into a pre-warmed clean cage to avoid hypothermia and monitored until they woke up and walked around. In vivo imaging on IVIS 100 series instrument was carried out as described. The results are summarized in FIG. 15, which show in vivo imaging of mice at 24 h post intracardiac injection of SP/pMV-CMV-Luc2 particles. The imaging data show high luciferase expression in the lungs, the same distribution pattern as the intravenously injected nanoparticles. No luminescence was detected in the liver.

Example 18. In Vivo Transfection by Intraperitoneal Injection

Figure 16A:
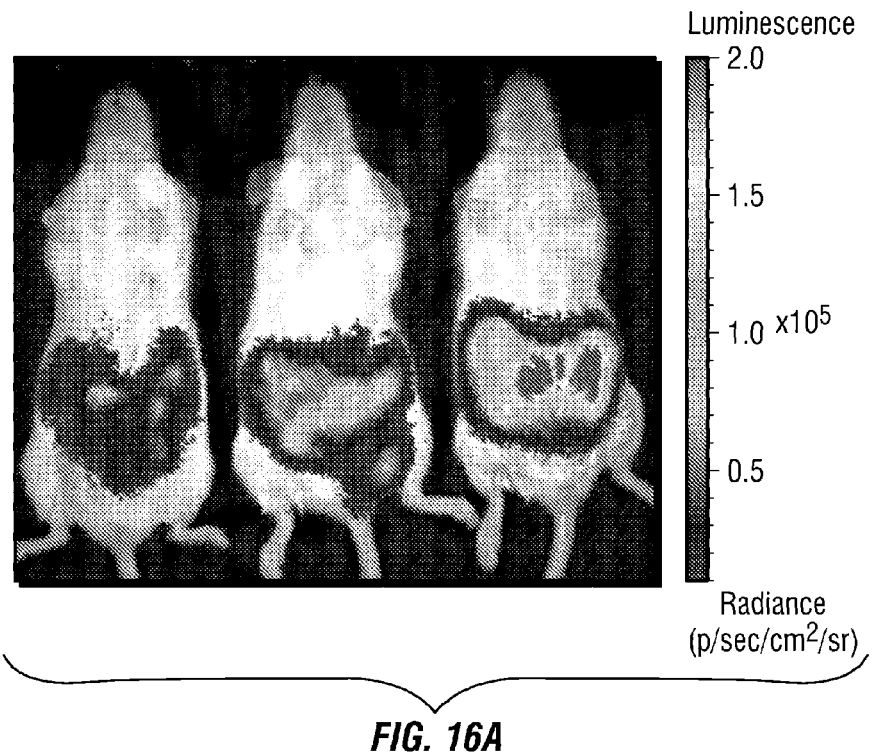
FIG. 16 shows in vivo images (FIG. 16A) and tissue images (FIG. 16B) from mice that were intraperitoneally injected with SP/pMV-CMV-Luc2 particles at N/P ratios of 10 (80 µg). The images were taken 20 h post administration.
Figure 16B:
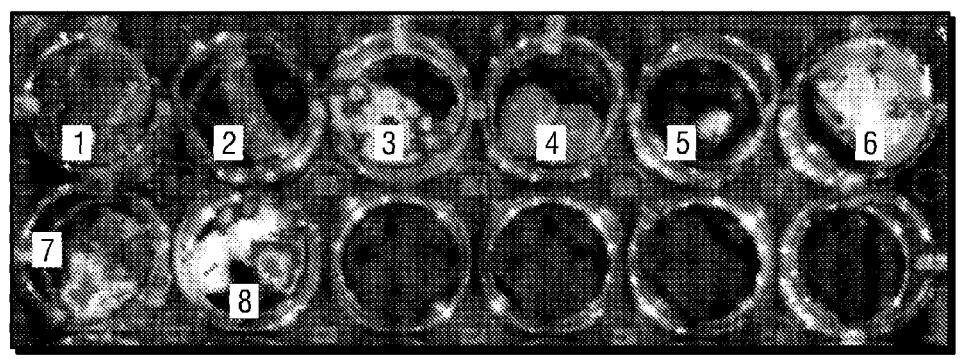

The mice from Example 16 were intraperitoneally injected with SP/pMV-CMV-Luc2 particles prepared at N/P ratios of 10, with plasmid dosed at 80 µg. Imaging of each mouse was obtained on an IVIS 100 series instrument after injection of D-luciferin (200 µL, 12.5 mg/mL) at 24 h post injection. The results are summarized in FIG. 16. The results indicate that SP/pMV-CMV-Luc2 is able to efficiently transfect intraperitoneal organs, and pancreas in particular.

Example 19. Immunohistochemistry Assay

Mice were sacrificed at 24 h post intravenous administration of SP/pMV-CMV-Luc2 particles containing 40 µg of plasmid. The lungs were taken out, embedded in OCT compound and snap frozen. The frozen tissue were cut into 4~8 µm thick cryostat sections and mounted on superfrost plus slides. Immunostaining for firefly luciferase was performed following standard protocol by using the rabbit anti-luciferase antibody (Abcam, USA). The mice injected with PBS were used as negative control.

Figure 17:
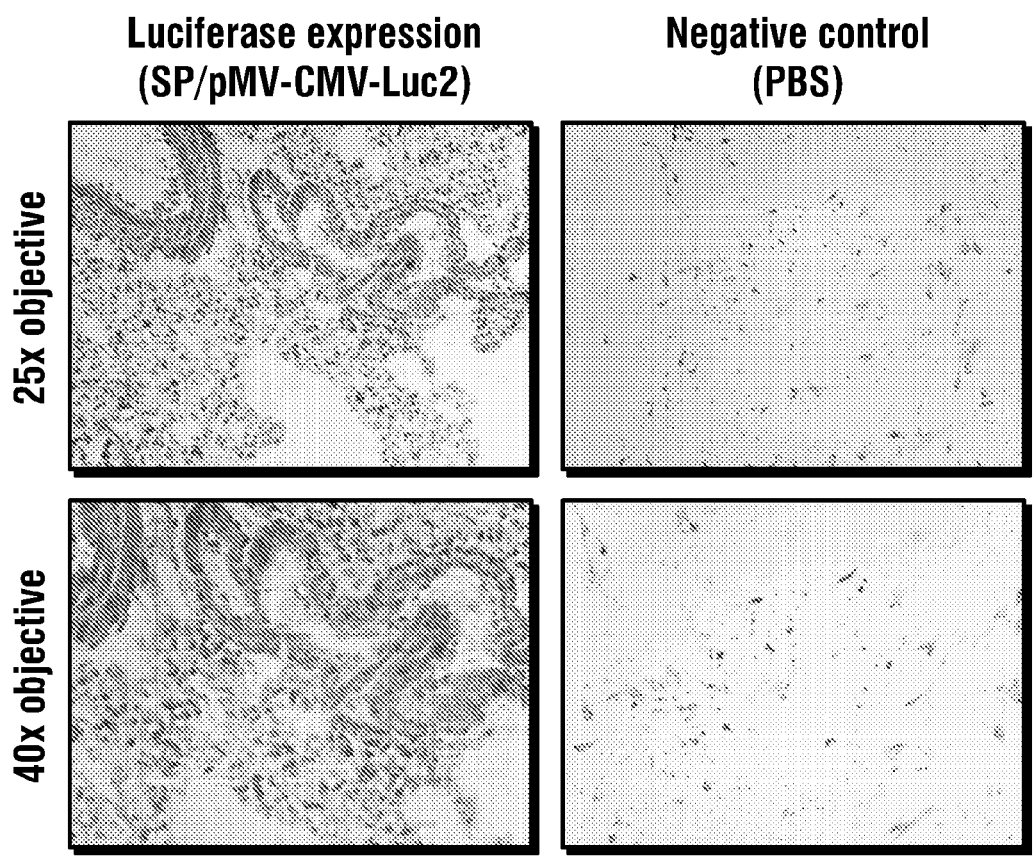
FIG. 17 shows histological results of the lung tissues from mice that were intravenously injected with SP/pMV-CMV-Luc2 (left) or PBS (right).

The results are shown in FIG. 17. Luciferase expressing cells are indicated with brown color blue nuclei. The figure shows strong expression of luciferase everywhere, especially in the blood vessels, as a result from SP-based gene delivery. No luciferase expression is detected from the negative control sample Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A composition for nucleic acid delivery into cells, wherein the composition comprises:
   a cationic polymer unit comprising a linker and a plurality of polymeric arms associated with the linker,
   wherein the plurality of polymeric arms comprise at least about 8 polymeric arms,
   wherein the plurality of polymeric arms comprise poly(aspartic acid) derivatives, and
   wherein the polymeric arms are branched from the linker to form a dendritic shape; and
   a nucleic acid associated with the cationic polymer unit.

2. The composition of claim 1, wherein the linker is covalently associated with the plurality of polymeric arms.

3. The composition of claim 1, wherein the linker is selected from the group consisting of small molecules, macromolecules, nanoparticles and combinations thereof.

4. The composition of claim 1, wherein the poly(aspartic acid) derivatives comprise from about 2 units to about 500 units of aspartic acid derivatives.

5. The composition of claim 1, wherein the poly(aspartic acid) derivatives comprise amine-modified aspartic acid derivatives (amine-modified poly(aspartic acid)).

6. The composition of claim 1, wherein the poly(aspartic acid) derivatives comprise diethylenetriamine-modified aspartic acid derivatives (PAsp(DET)$_n$).

7. The composition of claim 6, wherein n is an integer ranging from about 2 to about 500.

8. The composition of claim 1, wherein the poly(aspartic acid) derivatives are selected from the group consisting of amine-modified poly(aspartic acid), (PAsp(DET)$_n$), where n ranges from about 2 to about 500, PAsp(DET)$_{100}$, PAsp(DET)$_{70}$, PAsp(DET)$_{200}$, and combinations thereof.

9. The composition of claim 1, wherein the plurality of polymeric arms comprise about 8 branches of PAsp(DET)$_{30}$ (8-arm PAsp(DET)$_{30}$).

10. The composition of claim 1, wherein the cationic polymer unit is biodegradable.

11. The composition of claim 1, wherein the nucleic acid is selected from the group consisting of DNA, RNA, siRNA, shRNA, miRNA, analogues thereof, and combinations thereof.

12. The composition of claim 1, wherein the nucleic acid comprises plasmid DNA.

13. The composition of claim 1, wherein the nucleic acid comprises a gene.

14. The composition of claim 1, wherein the nucleic acid is associated with the cationic polymer unit through electrostatic interactions.

15. The composition of claim 1, wherein the composition has an N/P ratio from about 1 to about 40.

16. A method of delivering a nucleic acid into cells, wherein the method comprises introducing into the cells a composition comprising:
   a cationic polymer unit comprising a linker and a plurality of polymeric arms associated with the linker,
   wherein the plurality of polymeric arms comprise at least about 8 polymeric arms,
   wherein the plurality of polymeric arms comprise poly(aspartic acid) derivatives, and
   wherein the polymeric arms are branched from the linker to form a dendritic shape; and
   a nucleic acid associated with the cationic polymer unit.

17. The method of claim 16, wherein the poly(aspartic acid) derivatives are selected from the group consisting of amine-modified poly(aspartic acid), (PAsp(DET)$_n$), where n ranges from about 2 to about 500, PAsp(DET)$_{100}$, PAsp(DET)$_{70}$, PAsp(DET)$_{200}$, and combinations thereof.

18. The method of claim 16, wherein the plurality of polymeric arms comprise about 8 branches of PAsp(DET)$_{30}$ (8-arm PAsp(DET)$_{30}$).

19. The method of claim 16, wherein the cationic polymer unit is biodegradable.

20. The method of claim 16, wherein the nucleic acid is selected from the group consisting of DNA, RNA, siRNA, shRNA, miRNA, analogues thereof, and combinations thereof.

21. The method of claim 16, wherein the nucleic acid comprises plasmid DNA.

22. The method of claim 16, wherein the nucleic acid comprises a gene.

23. The method of claim 16, wherein the nucleic acid is associated with the cationic polymer unit through electrostatic interactions.

24. The method of claim 16, wherein the composition has an N/P ratio from about 1 to about 40.

25. The method of claim 16, wherein the method occurs in vivo in a subject.

26. The method of claim 25, wherein the subject is a human being.

27. The method of claim 25, wherein the composition is introduced into the cells of the subject by a method selected from the group consisting of oral administration (including gavage), inhalation, subcutaneous administration (sub-q), intravenous administration (I.V.), intraperitoneal administration (I.P.), intramuscular administration (I.M.), intrathecal injection, intratracheal injection, ocular injection, intradermal injection, intracardiac injection, intrathoracic injection, intracerebral injection, and combinations thereof.

28. The method of claim 16, wherein the method occurs in vitro.

29. The method of claim 16, wherein the composition is introduced into cells in vitro by transfection.

\* \* \* \* \*